US011279008B2

(12) United States Patent
Bethoux et al.

(10) Patent No.: US 11,279,008 B2
(45) Date of Patent: Mar. 22, 2022

(54) AUTOMATIC SCREW DRIVER WITH SCREW CARTRIDGE

(71) Applicant: Stryker European Operations Holdings, LLC, Wilmington, DE (US)

(72) Inventors: Nicolas F. Bethoux, Ringwood, NJ (US); Rebekah Brougher, Caulfield (AU); Michael Herron, Mountain View, CA (US); Kristen Yardley, Lenexa, KS (US)

(73) Assignee: Stryker European Operations Holdings, LLC, Wilmington, DE (US)

( * ) Notice: Subject to any disclaimer, the term of this patent is extended or adjusted under 35 U.S.C. 154(b) by 319 days.

(21) Appl. No.: 16/502,424

(22) Filed: Jul. 3, 2019

(65) Prior Publication Data

US 2020/0009710 A1    Jan. 9, 2020

Related U.S. Application Data

(60) Provisional application No. 62/694,180, filed on Jul. 5, 2018.

(51) Int. Cl.
*B25B 23/04* (2006.01)
*A61B 17/88* (2006.01)
(Continued)

(52) U.S. Cl.
CPC ........ *B25B 23/045* (2013.01); *A61B 17/8875* (2013.01); *B25B 21/002* (2013.01);
(Continued)

(58) Field of Classification Search
CPC ....... B25B 23/045; B25B 23/02; B25B 23/04; B25B 23/06; B25B 23/08; B25B 21/002;
(Continued)

(56) References Cited

U.S. PATENT DOCUMENTS 2,219,484 A    10/1940 Lyon
3,656,520 A     4/1972 Caffa
(Continued)

FOREIGN PATENT DOCUMENTS

DE    210641 A1    6/1984
DE    3717959 A1   12/1988
(Continued)

OTHER PUBLICATIONS

European Search Report and Written Opinion from EP19184327 dated Dec. 6, 2019, pp. 1-8.

*Primary Examiner* — Robert J Scruggs
(74) *Attorney, Agent, or Firm* — Lerner, David, Littenberg, Krumholz & Mentlik, LLP

(57) ABSTRACT

An implant magazine for use with a driver includes a plurality of implants, an implant carrier defining a plurality of apertures, each implant of the plurality of implants being disposed within an aperture of the plurality of apertures, wherein an implant is disengaged from the implant carrier upon application of a predetermined force applied to the implant, and a base defining a cavity in which the implant carrier and the plurality of implants are disposed. A cartridge for use with a driver includes the implant magazine, a housing in which the implant magazine is disposed, and a blade having a longitudinal axis and being at least partially and rotatably disposed within the housing. A kit includes a driver, a motor, and the cartridge configured for cooperation with the driver to be operated by the motor. A method of using the driver includes inserting an implant into a medium.

18 Claims, 21 Drawing Sheets

(51) Int. Cl.
  *B25B 21/00* (2006.01)
  *B25B 23/06* (2006.01)
  *B25B 23/08* (2006.01)
  *F16B 27/00* (2006.01)

(52) U.S. Cl.
  CPC .............. *B25B 23/06* (2013.01); *B25B 23/08* (2013.01); *F16B 27/00* (2013.01)

(58) Field of Classification Search
  CPC ... A61B 17/8875; A61B 17/58; A61B 17/861; A61B 17/865; A61B 17/1615; A61B 17/1624; A61B 17/1671; A61B 17/7082; F16B 27/00; B23P 19/004; B23P 19/06; B23P 19/003
  See application file for complete search history.

(56) References Cited

U.S. PATENT DOCUMENTS

| | | | |
|---|---|---|---|
| 4,007,834 A | | 2/1977 | Borgersen |
| 4,926,719 A | * | 5/1990 | Kross .................. B25B 23/045 221/25 |
| 4,936,169 A | | 6/1990 | Parsons |
| 5,445,641 A | | 8/1995 | Frigg et al. |
| 6,502,484 B2 | | 1/2003 | Pao-Hsi |
| 6,813,977 B2 | * | 11/2004 | Goodhue ................ B25B 23/04 227/137 |
| 6,988,303 B2 | | 1/2006 | Goodhue et al. |
| 7,091,683 B1 | | 8/2006 | Smith et al. |
| 7,258,046 B2 | | 8/2007 | Fruhm et al. |
| 7,562,800 B2 | | 7/2009 | Goodhue et al. |
| 7,565,852 B2 | | 7/2009 | Yu |
| 7,771,429 B2 | | 8/2010 | Ballard et al. |
| 8,087,325 B2 | | 1/2012 | Neubardt |
| 8,262,669 B2 | | 9/2012 | Walker |
| 8,377,074 B2 | | 2/2013 | Garcia et al. |
| 8,414,594 B2 | * | 4/2013 | Berger ............... A61B 17/1728 606/104 |
| 8,534,164 B2 | | 9/2013 | Watt |
| 8,943,927 B2 | | 2/2015 | Watt |
| 9,265,551 B2 | | 2/2016 | Kust et al. |
| 9,271,732 B2 | * | 3/2016 | Walker ................. A61B 17/861 |
| 9,284,110 B2 | | 3/2016 | Garcia et al. |
| 9,616,557 B2 | | 4/2017 | Hays et al. |
| 9,833,884 B2 | | 12/2017 | Andriolo et al. |
| 2003/0037313 A1 | | 2/2003 | Halpern et al. |
| 2006/0053986 A1 | | 3/2006 | Ward |
| 2011/0064978 A1 | | 3/2011 | McGahan et al. |
| 2014/0309702 A1 | | 10/2014 | Wand |

FOREIGN PATENT DOCUMENTS

| | | |
|---|---|---|
| DE | 102008010333 A1 | 8/2009 |
| DE | 102014102907 A1 | 10/2014 |
| EP | 512262 B1 | 7/1995 |
| EP | 2489473 A2 | 8/2012 |
| EP | 2507017 B1 | 3/2014 |
| EP | 2730375 A2 | 5/2014 |
| EP | 3141351 A1 | 3/2017 |
| EP | 3184260 A1 | 6/2017 |
| WO | 0007510 A1 | 2/2000 |
| WO | 03009097 A2 | 1/2003 |
| WO | 03090974 A1 | 11/2003 |
| WO | 03101322 A1 | 12/2003 |
| WO | 2013127406 A1 | 9/2013 |
| WO | 2015009850 A1 | 1/2015 |
| WO | 2018005714 A1 | 1/2018 |

* cited by examiner

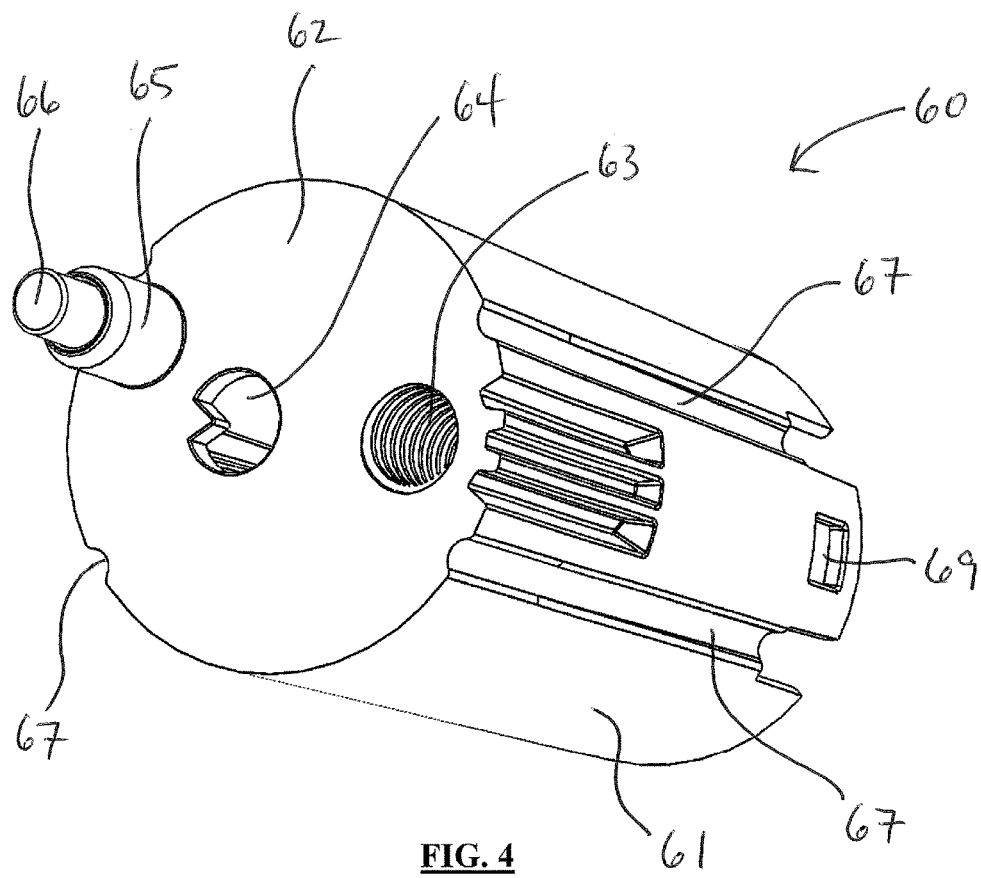
FIG. 4
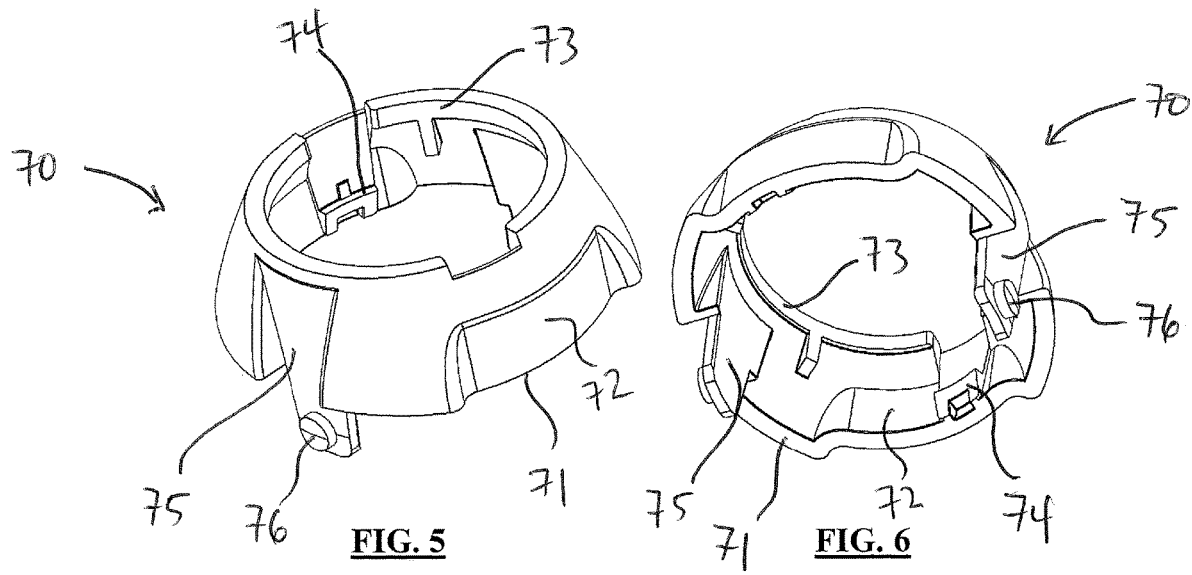
FIG. 5      FIG. 6

AUTOMATIC SCREW DRIVER WITH SCREW CARTRIDGE

CROSS-REFERENCE TO RELATED APPLICATIONS

The present application claims the benefit of the filing date of U.S. Provisional Patent Application No. 62/694,180 filed Jul. 5, 2018, the disclosure of which is hereby incorporated herein by reference.

BACKGROUND OF THE INVENTION

The present invention relates to drivers and methods of using such tools, for example in the surgical field. More particularly, the present invention relates to a surgical driver having a removable cartridge that facilitates secure and reliable loading of a plurality of implants such as screws in series, as well as the methods associated with using the driver.

Existing prior art drivers that include screw cartridges feature many moving parts that ultimately negatively affect precision and the longevity of the devices. Devices that allow the reloading of screws typically require the screws to be shuttled within the device before being seated on the end of the driver for insertion. Each time a device is indexed to load a new screw, the driver must cycle all of its components to facilitate loading. This overuse of components more quickly exhausts the lifetime cycles that can be performed by certain components, leading to replacement of intricate parts and ultimately failure of the drivers to maintain a high level of performance Prior art devices also present difficulty to the user in being able to quickly reload and understand how many screws or workpieces are left during use of a particular cartridge.

Thus, there exists a need for a driver and method of its use that improves upon these and other shortcomings of the prior art.

BRIEF SUMMARY OF THE INVENTION

A first aspect of the present invention is an implant magazine for use with a driver, the implant magazine including a plurality of implants, an implant carrier defining a plurality of apertures, each implant of the plurality of implants being disposed within an aperture of the plurality of apertures, wherein an implant is disengaged from the implant carrier upon application of a predetermined force applied to the implant, and a base defining a cavity in which the implant carrier and the plurality of implants are disposed.

In accordance with other embodiments of the first aspect, each aperture in the implant carrier may be defined by one or more deformable fins configured to contact the implant. The plurality of implants may be a plurality of screws. The implant magazine may further include an indexing spring to rotate the implant carrier within the base, wherein the indexing spring is loaded to rotate the implant carrier about one complete revolution of the implant carrier so that each implant of the plurality of implants is disposed at different times adjacent an aperture in the base through which an implant can be passed. The implant magazine may further include a lid defining a plurality of apertures through which the plurality of implants are accessible, and a rotor connectable with the lid for housing the implant carrier. The lid may define a chamfered circumferential surface at the first aperture beneath which the first implant is recessed. The base may be translucent to allows a user to view the presence of the plurality of implants within the implant magazine.

A cartridge for use with a driver may include the implant magazine as described above, a housing in which the implant magazine is disposed, and a blade having a longitudinal axis and being at least partially and rotatably disposed within the housing, wherein the blade has a working configuration and a loading configuration, wherein in the working configuration, rotation of the blade causes rotation of an implant of the plurality of implants and does not move the housing along the longitudinal axis of the blade, and wherein in the loading configuration, rotation of the blade moves the housing and the implant magazine along the longitudinal axis of the blade.

A proximal end of the housing may have an aperture, and the cartridge may further include an extension screw having a head and a shaft disposed within the aperture of the housing, wherein the extension screw defines a lumen through the head and the shaft, and the blade is at least partially disposed within the lumen of the extension screw. The aperture of the housing may be internally threaded and the shaft of the extension screw is threaded and threadably connected to the aperture of the housing, and wherein the lumen of the extension screw may have a noncircular cross-section in the head of the extension screw and the blade has a noncircular collar configured to engage the noncircular cross-section of the lumen. In the working configuration, the collar may be disengaged from the lumen to allow relative rotation between the blade and the extension screw such that the blade rotates with respect to the extension screw, and in the loading configuration, the collar may be engaged with the lumen to prevent relative rotation between the blade and the extension screw to thereby move the housing with respect to the extension screw as the threads of the threaded shaft of the extension screw engage the internally threaded aperture of the housing.

The cartridge may further include a blade lock having a flange and a longitudinal body extending distally from the flange, the flange defining a key-hole shaped aperture through which the blade is disposed, wherein the key-hole shaped aperture in the flange has a first portion with a first diameter and a second portion with a second diameter smaller than the first diameter. The second diameter of the key-hole shaped aperture in the flange may be smaller than an outer diameter of the collar of the blade, and the first diameter of the key-hole shaped aperture in the flange may be larger than the outer diameter of the collar of the blade. The collar of the blade may be configured to pass through the first portion of the key-hole shaped aperture in the flange but not through the second position of the key-hole shaped aperture in the flange. The proximal end of the housing may have a non-circular aperture, and the longitudinal body of the blade lock may have a non-circular cross-section along at least a portion of its length that is substantially matched to the non-circular aperture. The non-circular cross section of the body of the blade lock may be defined by a circumferential arc and a V-shaped notch. A location of the V-shaped notch about an axis of the body of the blade lock may vary along at least a portion of the axis, whereby the non-circular cross-section of the body defines a cam surface. The cam surface may force either the first portion or the second portion of the key-hole shaped aperture into alignment with the internally-threaded aperture of the housing.

The cartridge may further include an outer housing in which the housing is movable. The outer housing may include internal longitudinal ribs that cooperate with external longitudinal grooves on the housing to guide movement of the housing with respect to the outer housing. The threaded shaft of the extension screw may be disposed within an aperture in a proximal end of the outer housing having a diameter smaller than a maximum diameter of the head of the extension screw, whereby the extension screw is rotatable but not translatable with respect to the outer housing.

The base of the implant magazine may include external ribs for engagement with recesses inside the outer housing of the cartridge. The cartridge may further include a rear cover defining an aperture through which a proximal end of the blade extends. The blade may have a distal working end having a wedge for cooperation with a head of an implant, and a tip extending from a distal surface of the wedge. The wedge of the blade may be configured to engage a similarly configured recess in the head of the implant to temporarily hold the implant to the blade.

A kit may include a driver, a motor, and the cartridge described above and configured for cooperation with the driver to be operated by the motor. The driver may define a cavity in which the cartridge is disposed in a working condition. The cartridge may further include a magnet and the driver may include an analog hall sensor that communicates with the magnet to detect the location of the housing with respect to the cavity of the driver. The cartridge may further include a magnet and the driver may include a digital hall sensor that communicates with the magnet to detect the presence of the cartridge with respect to the cavity of the driver. The cartridge may further include an outer housing in which the housing is movable, and the kit may further include a twist lock cap configured to secure the outer housing of the cartridge to the driver.

A second aspect of the present invention is a cartridge for use with an implant magazine and a driver, the cartridge including a housing in which the implant magazine is disposed, and a blade having a longitudinal axis and being at least partially and rotatably disposed within the housing. The blade may have a working configuration and a loading configuration, wherein in the working configuration, rotation of the blade causes rotation of an implant and does not move the housing along the longitudinal axis of the blade, and wherein in the loading configuration, rotation of the blade moves the housing and the implant magazine along the longitudinal axis of the blade. In accordance with other embodiments of the second aspect, the cartridge may be provided as described above in connection with the first aspect.

A third aspect of the present invention is a method of using a driver, the method including loading an implant magazine having a plurality of implants into a housing of a cartridge, the implant magazine including an implant carrier defining a plurality of apertures, each implant of the plurality of implants being disposed within an aperture of the plurality of apertures, operating a driver to control the cartridge such that a distal end of a blade of the cartridge is advanced distally relative to the housing of the cartridge and into engagement with a first implant of the plurality of implants located in a first aperture of the plurality of apertures, inserting the first implant into a medium, and withdrawing the distal end of the blade proximally relative to the housing and through the first aperture to allow the implant carrier to rotate about a central axis thereof until a next adjacent aperture of the plurality of apertures is located distally in front of the blade.

In accordance with other embodiments of the third aspect, the step of operating may further include disengaging the first implant from the implant carrier by applying a predetermined force to the first implant from the distal end of the blade. The step of operating may further include deforming one or more fins defining the first aperture of the implant carrier by applying a predetermined force to the first implant from the distal end of the blade. The plurality of implants may be a plurality of screws, and the step of inserting may include inserting a first screw into tissue.

The step of withdrawing may further include allowing the implant carrier to rotate under the force of an indexing spring. The method may further include repeating, until a last of the plurality of implants is inserted into a medium, a sequence of: operating the driver to control the cartridge such that the distal end of the blade is advanced distally relative to the housing of the cartridge and into engagement with a next adjacent implant of the plurality of implants located in the next adjacent aperture of the plurality of apertures, inserting the next adjacent implant into a medium, and withdrawing the distal end of the blade proximally relative to the housing and through the next adjacent aperture to allow the implant carrier to rotate about the central axis thereof until a next adjacent aperture of the plurality of apertures is located distally in front of the blade, wherein the force of the indexing spring permits rotation of the implant carrier about substantially one complete revolution of the implant carrier.

The step of operating the driver may advance the distal end of the blade distally relative to the housing into contact with a surface of the implant magazine that is located proximally of the first implant in the first aperture to guide the distal end of the blade toward a center of the first aperture. The step of operating the driver may advance the distal end of the blade distally relative to the housing into contact with a surface of the implant magazine located proximally of the first implant in the first aperture to tilt the implant carrier about a second axis perpendicular to the central axis to disengage the implant carrier from a rotationally locked connection with the cartridge. The step of operating the driver may advance a portion of the implant carrier distally away from the housing of the cartridge to disengage protrusions on the implant carrier from a rotationally locked connection with ribs on the housing. When the next adjacent aperture of the plurality of apertures is located distally in front of the blade, a central axis of the next adjacent aperture and a central axis of the blade may not be exactly collinear. The step of withdrawing may result in the implant carrier automatically rotating until the next adjacent aperture is located distally in front of the blade.

The step of operating the driver may include maintaining an axial position of the blade with respect to the driver and moving the implant carrier proximally toward the driver. The step of withdrawing may include rotating the blade to rotate an extension screw of the cartridge having a head and a threaded shaft so that the extension screw moves the housing of the cartridge, the proximal end of the housing having an internally-threaded aperture engaged with the threaded shaft of the extension screw. The step of inserting may include operating the blade in a working configuration in which rotation of the blade causes rotation of the first implant of the plurality of implants and does not advance the blade relative to the housing. The step of operating may include operating the blade in a loading configuration in which rotation of the blade causes advancement of the blade relative to the housing and the implant magazine. During at least a portion of the step of withdrawing, movement of the housing may rotate a blade lock of the cartridge into connection with the blade to maintain the blade in the loading configuration. The blade lock may have a cam surface that automatically moves it into connection with the blade during loading of an implant onto the distal end of the blade.

The step of operating the driver may include engaging the first implant by engaging a wedge of the blade with a similarly configured recess in the head of the first implant to temporarily hold the first implant to the blade. The method may further include loading the cartridge into a cavity of the driver. The method may further include securing the cartridge within the driver with a twist lock cap.

BRIEF DESCRIPTION OF THE DRAWINGS

FIG. 4 is a perspective proximal view of the extension housing of the screw cartridge shown in FIG. 1A.

FIGS. 5 and 6 are perspective distal and proximal views, respectively, of a twist lock of the screw cartridge shown in FIG. 1A.

DETAILED DESCRIPTION

Figure 1A:
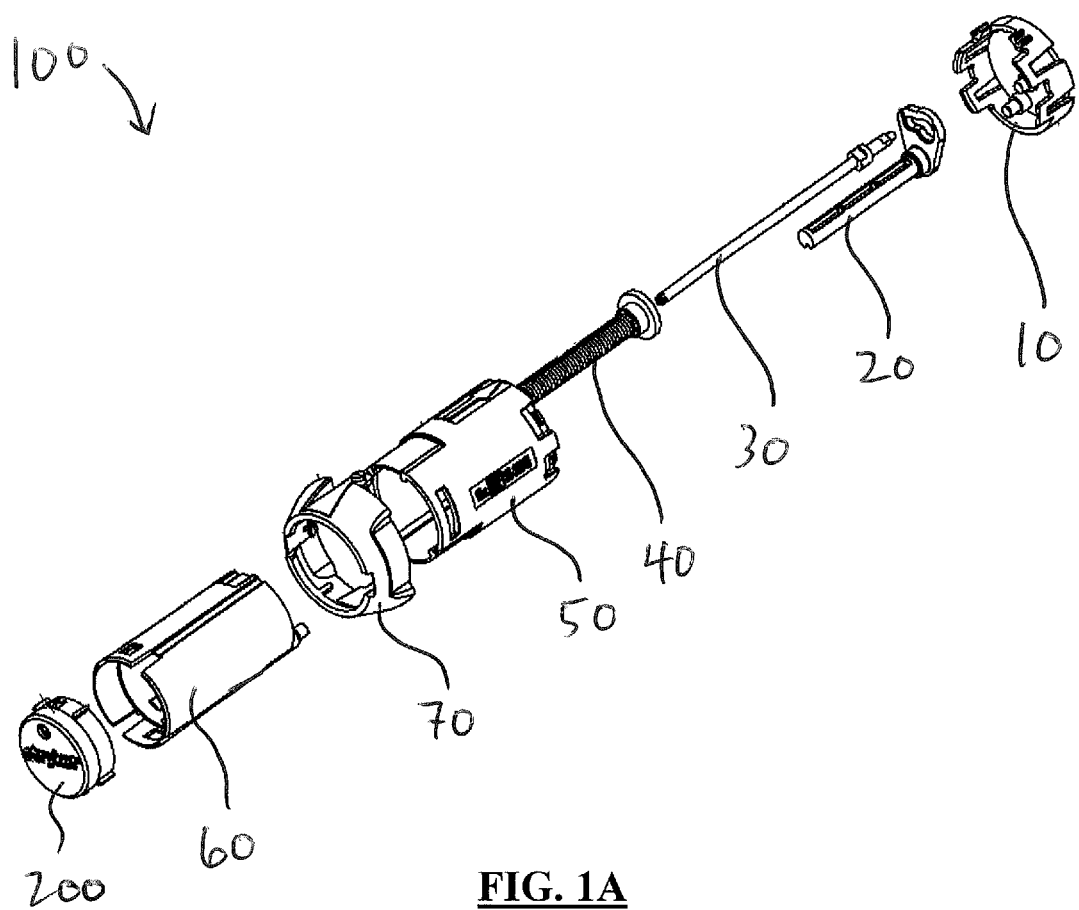
FIGS. 1A and 1B are perspective exploded and assembly views, respectively, of a screw cartridge in accordance with one embodiment of the present invention.
Figure 1B:
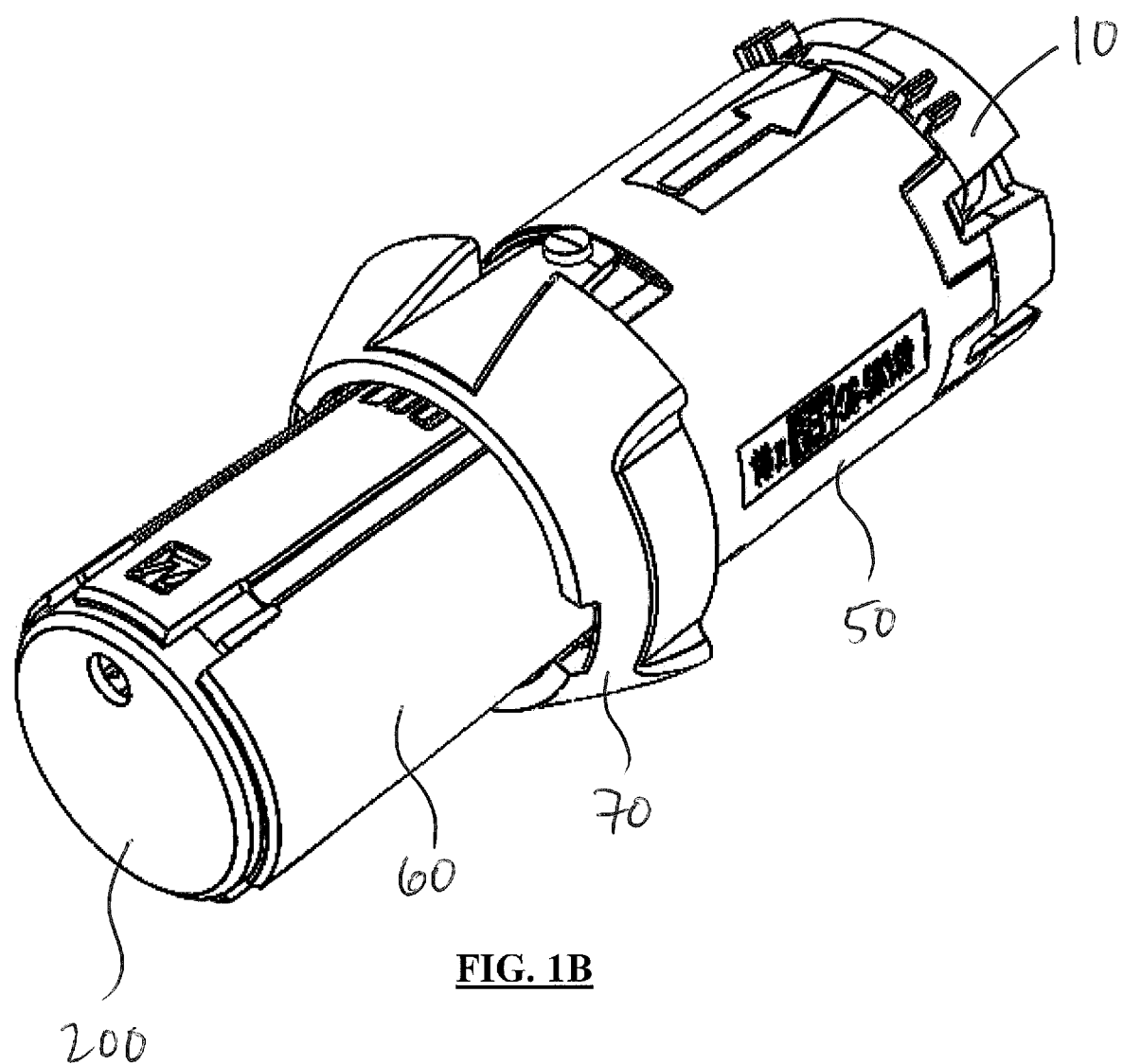
Figure 1C:
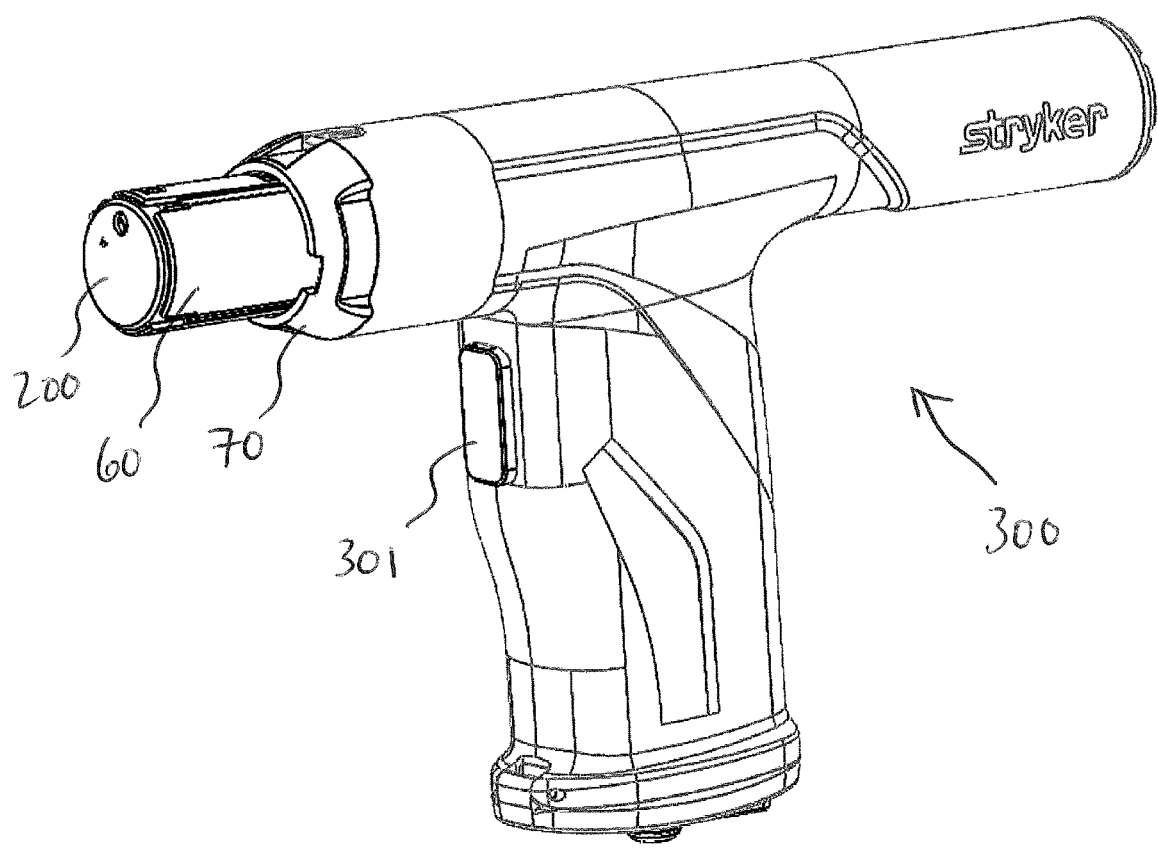
FIG. 1C is a perspective view of the screw cartridge shown in FIG. 1A loaded into a driver.

As shown in FIGS. 1A-C, a first embodiment in accordance with the present invention is a screw cartridge 100 for use with an automated driver 300 having a handle by which to grip and use the device. Driver 300 is one possible embodiment of a driver; other configurations and geometries of drivers could also be used that perform the same functionality with the screw cartridge 100. Screw cartridge 100 is shown in exploded view in FIG. 1A and includes a rear cover assembly 10, a blade lock 20, a driver blade 30, an extension screw 40, an outer housing 50, an extension housing 60, a screw magazine assembly 200 in which several screws 230 are assembled, and a twist lock 70.

While driver 300, cartridge 100, and magazine assembly 200 are described in connection with the depicted embodiment as being used with screws 230, driver 300, cartridge 100, and magazine assembly 200 can be used with many types of implants. Some examples of implants that can be inserted with the present system are nails, anchors, plugs, rivets, etc. Non-surgical use of the present components can focus on insertion of such elements into wood, drywall, metal, or other mediums. Surgical applications can insert surgical screws, surgical nails, suture anchors, etc. In one such embodiment, a plurality of suture anchors each respectively connected with one of a plurality of sutures can be inserted. In another embodiment, a plurality of suture anchors each connected to a single suture at different locations along the suture can be inserted. The present driver 300, cartridge 100, and magazine assembly 200 have broad applicability in and outside of the surgical field and with any type of implant for which sequential insertion into a medium is desired.

Figure 2:
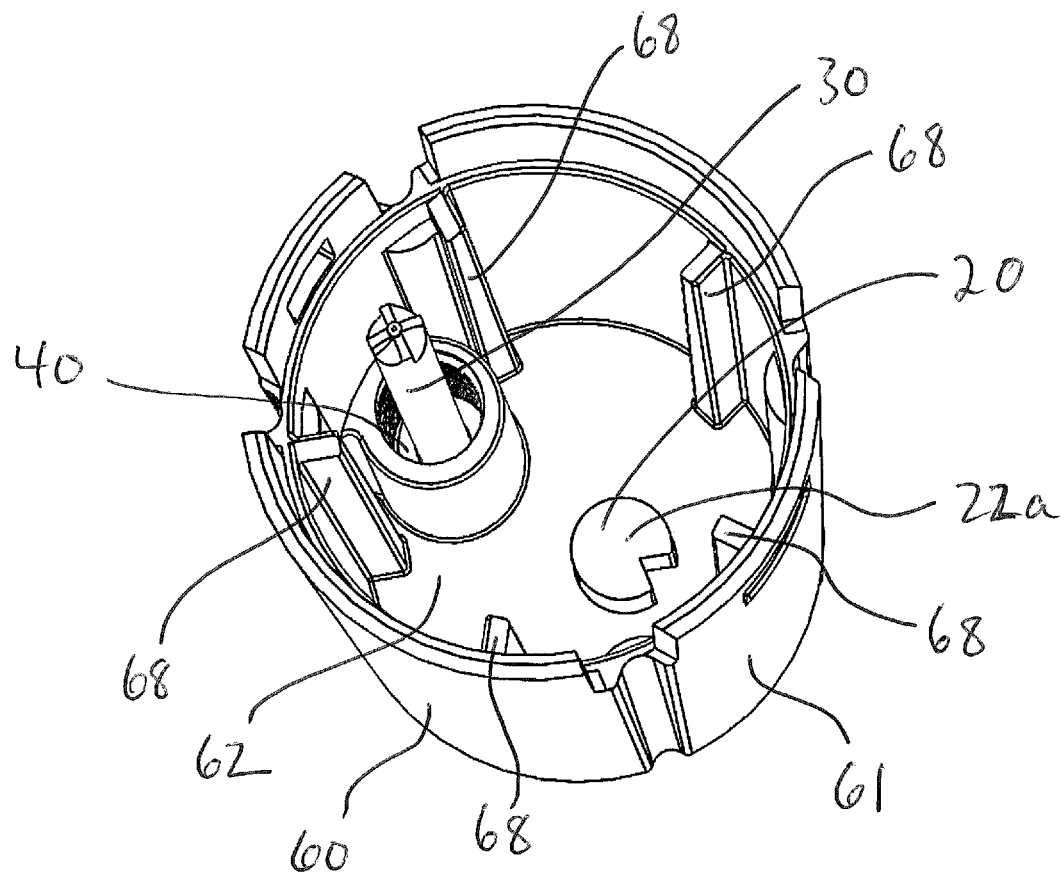
FIGS. 2 and 3 are perspective distal and proximal assembly views, respectively, of a blade lock, a driver blade, an extension screw, and an extension housing of the screw cartridge shown in FIG. 1A.
Figure 3:
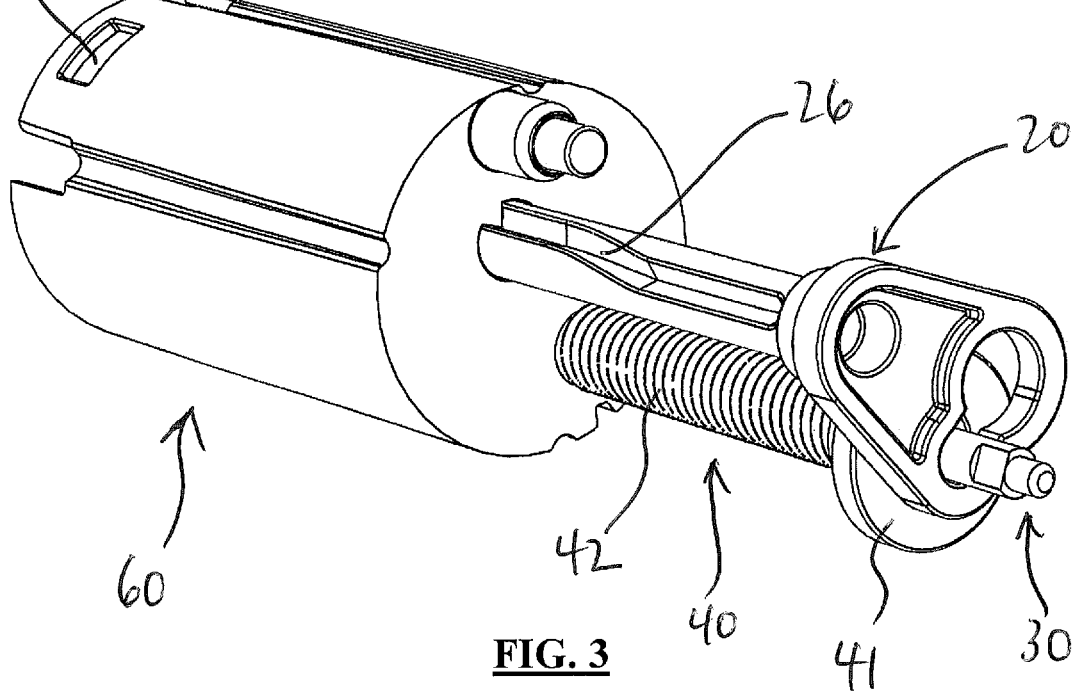
Figure 7:
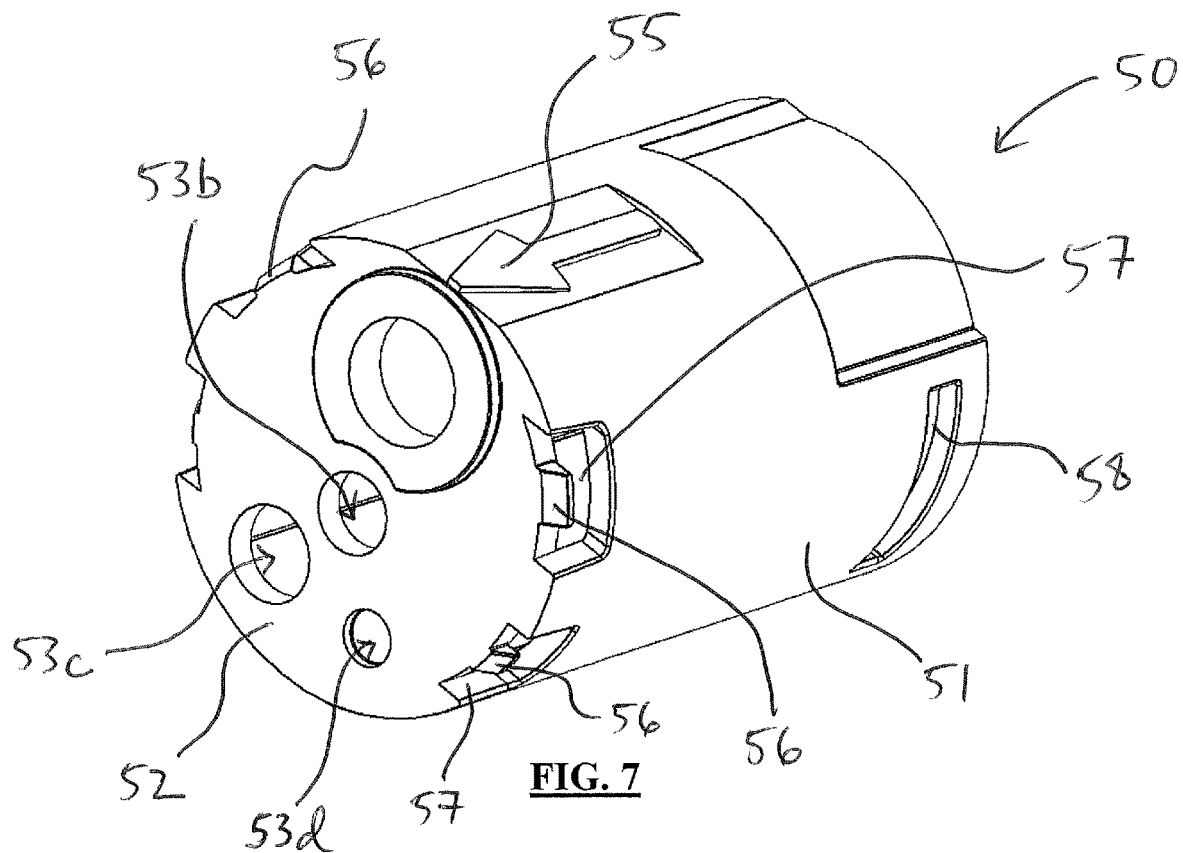
FIGS. 7 and 8 are perspective proximal and distal views, respectively, of an outer housing of the screw cartridge shown in FIG. 1A.
Figure 8:
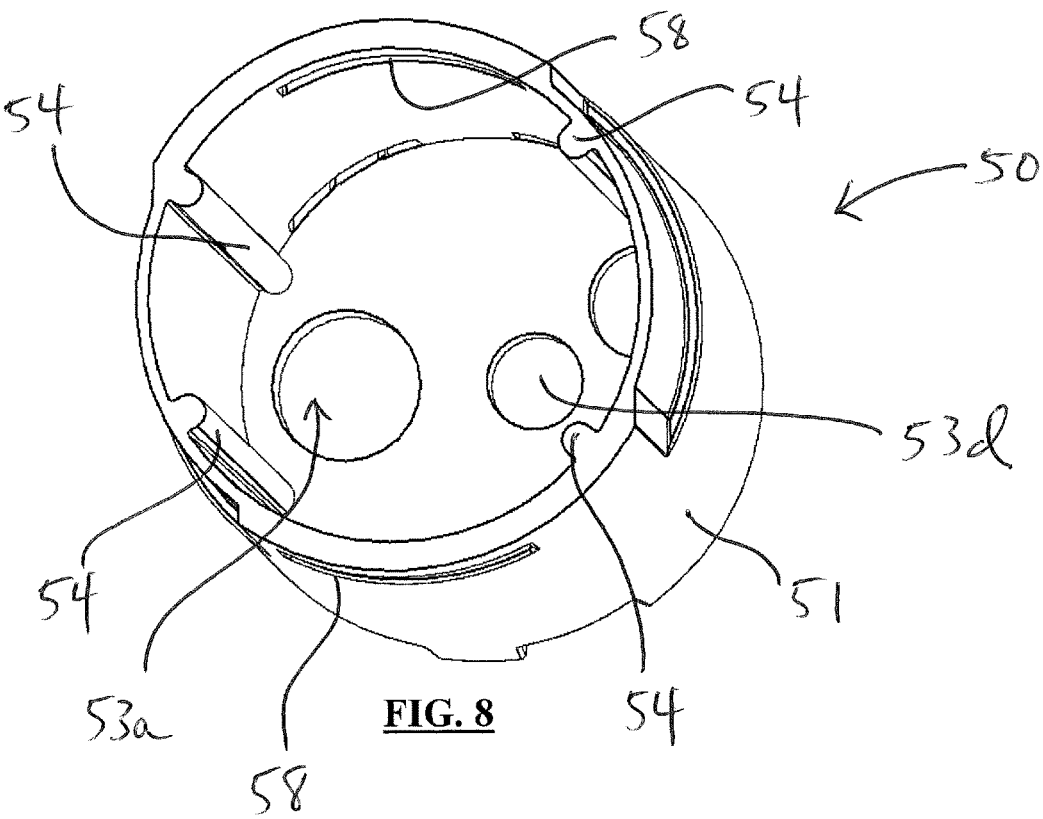

As shown in FIGS. 2-4, extension housing 60 includes a generally cylindrical sidewall 61 and a proximal end wall 62. Extension housing 60 is open at its distal end to define a cavity therein. Proximal end wall 62 defines a threaded aperture 63 through which extension screw 40 and driver blade 30 are positioned, and a non-circular aperture 64 through which blade lock 20 is disposed. A boss 65 extends proximally from proximal end wall 62 and houses an extension housing magnet 66. An analog hall sensor disposed on a sensor board within driver 300 receives information about the location of extension housing 60 relative to the analog hall sensor by sensing the presence of extension housing magnet 66 in boss 65 in the extension housing 60. With this capability, driver 300 can sense when cartridge 100 is loaded therein, whether cartridge 100 is in its extended or retracted state, and when cartridge 100 is finished extending and retracting. When driver 300 detects that cartridge is in the correct position, it halts the extension or retraction accordingly. Since the analog hall sensor outputs variable voltage, the location of the analog magnet can be also defined so that driver 300 can distinguish between multiple different types of cartridges.

Grooves 67 extend along the length of an outer face of sidewall 61, while ribs 68 are disposed around the circumference of an inner surface of cylindrical sidewall 61 and extend along the length of an inner face of sidewall 61. One or more openings 69 are present in sidewall 61 near the distal end of extension housing 60 to each coordinate respectively with two groups of snap features 265, 266 on an outer surface of cylindrical sidewall 262 of screw magazine base 260, as explained below.

Figure 9A:
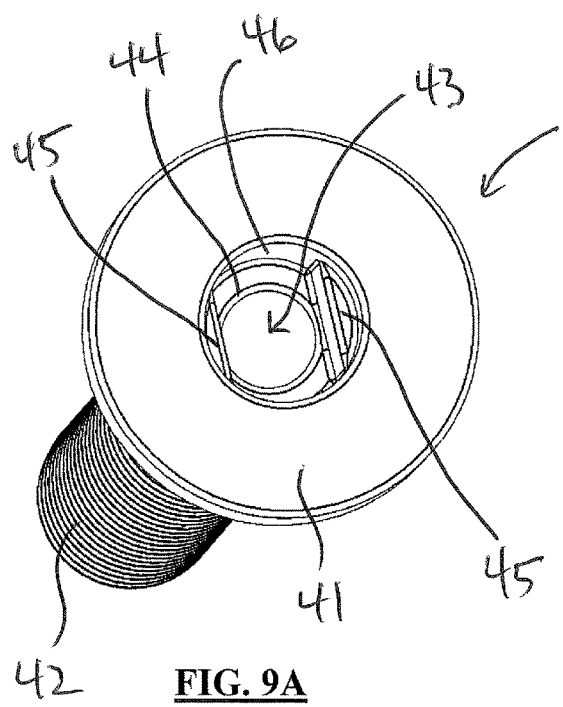
FIGS. 9A and 9B are perspective proximal and side elevational views, respectively, of the extension screw of the screw cartridge shown in FIG. 1A.
Figure 10:
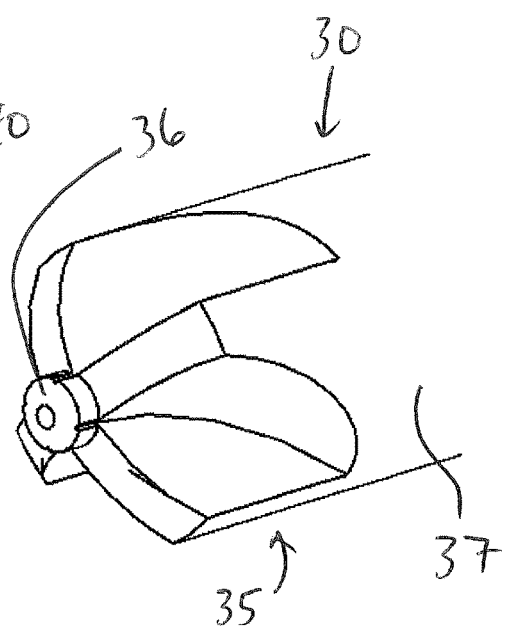
FIG. 10 is an enlarged view of a distal end of the driver blade of the screw cartridge shown in FIG. 1A.
Figure 9B:
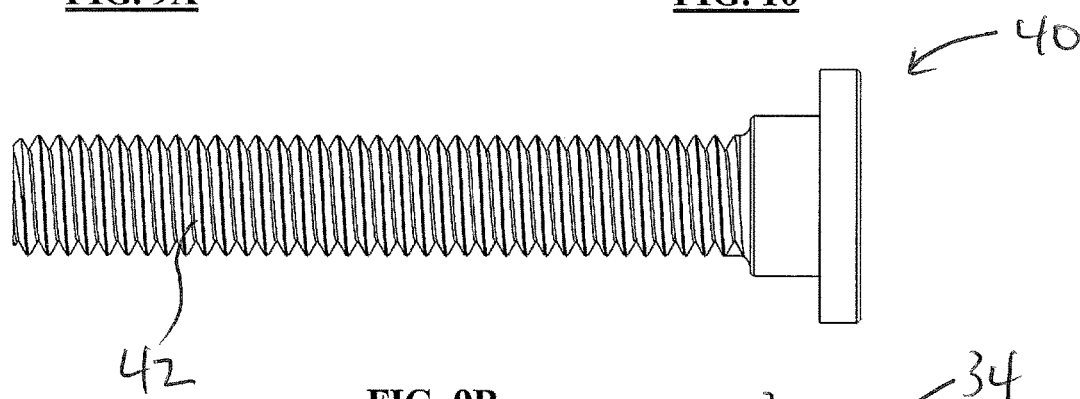
Figure 11:
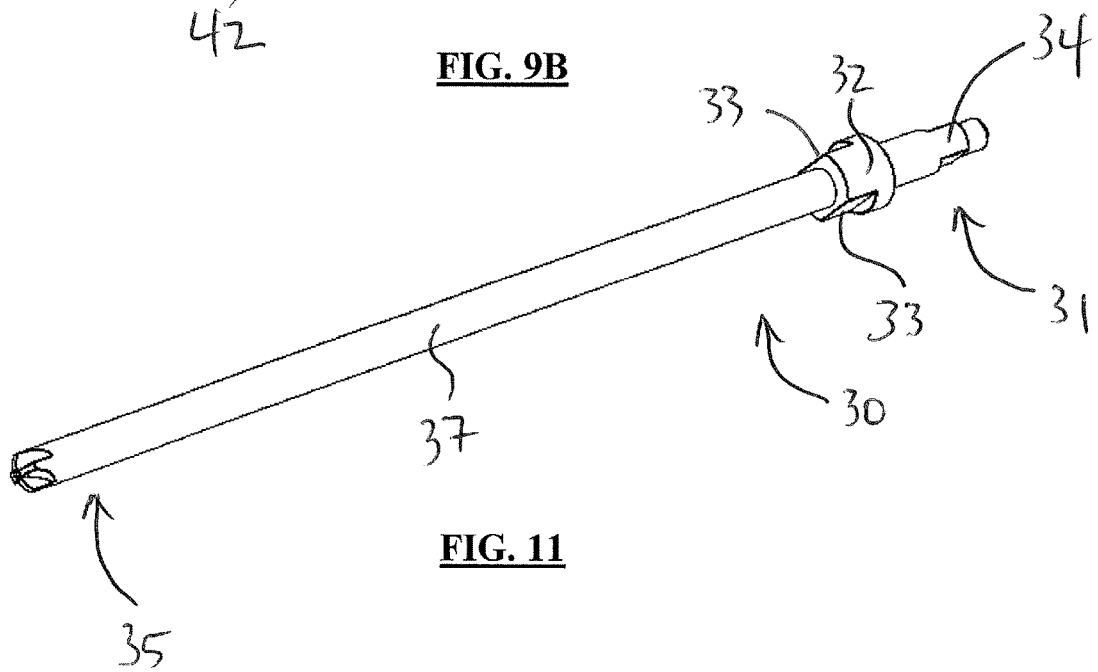
FIG. 11 is a perspective distal view of the driver blade of the screw cartridge shown in FIG. 1A.

Extension screw 40 is shown in FIGS. 3, 9A, and 9B, and includes a head 41 and a threaded shaft 42. A lumen 43 extends completely through head 41 and shaft 42 along the longitudinal axis of screw 40 so that it is open at both the proximal and distal ends of screw 40. A recess 44 extends distally into head 41 from a proximal face thereof. At least a portion of the depth of recess 44 has a non-circular cross section defined by a cylindrical wall 46 and two shoulders 45 that extend from cylindrical wall 46 into recess 44. Two shoulders 45 are shown, though one or more shoulders 45 could be used to create the non-circular cross-section of recess 44. The minimum diameter of cylindrical wall 46 is greater than an outer diameter of lumen, while the minimum distance between shoulders 45 is greater than or equal to the outer diameter of lumen 43.

Driver blade 30 is shown in FIGS. 1A, 2, 3, 10, and 11 and is a driver for the screws to be inserted by the system. A proximal end 31 of blade 30 has a collar 32 with flat side surfaces 33. Collar 32 is dimensioned to mate with recess 44 of extension screw 40, such that when collar 32 is engaged with recess 44, the noncircular configurations of each allow torque to be transferred from blade 30 to extension screw 40. This torque can be generated at a noncircular end 34 of blade 30, which is engaged by a rotational driver of the automated driver 300 so that it can be driven. Collar 32 can have one or more flat side surfaces 33 in coordination with recess 44. Proximal end 31 is spaced along a shaft 37 of blade 30 from a distal end 35 thereof, at which a working end is configured as a Philips-head screwdriver. A protrusion 36 extends distally at the apex of distal end 35 for engagement with a screw head, as described below. While a Philips-head is shown and described herein, any other working end could be employed, including a flat-head screwdriver, a hex-head screwdriver, or any other configuration of driver tip to cooperate with the head of a screw or other implant. A kit of driver blades all having different sizes and/or configurations of tips can be provided for use with the system to enhance modularity.

Figure 12:
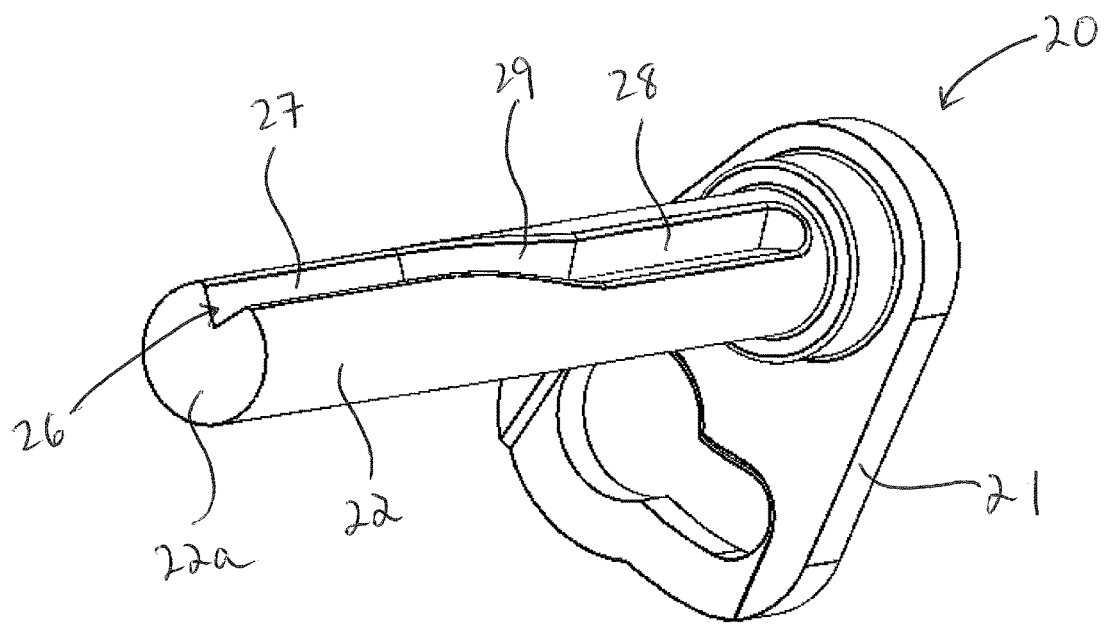
FIGS. 12 and 13 are perspective distal and proximal views, respectively, of the blade lock of the screw cartridge shown in FIG. 1A.
Figure 13:
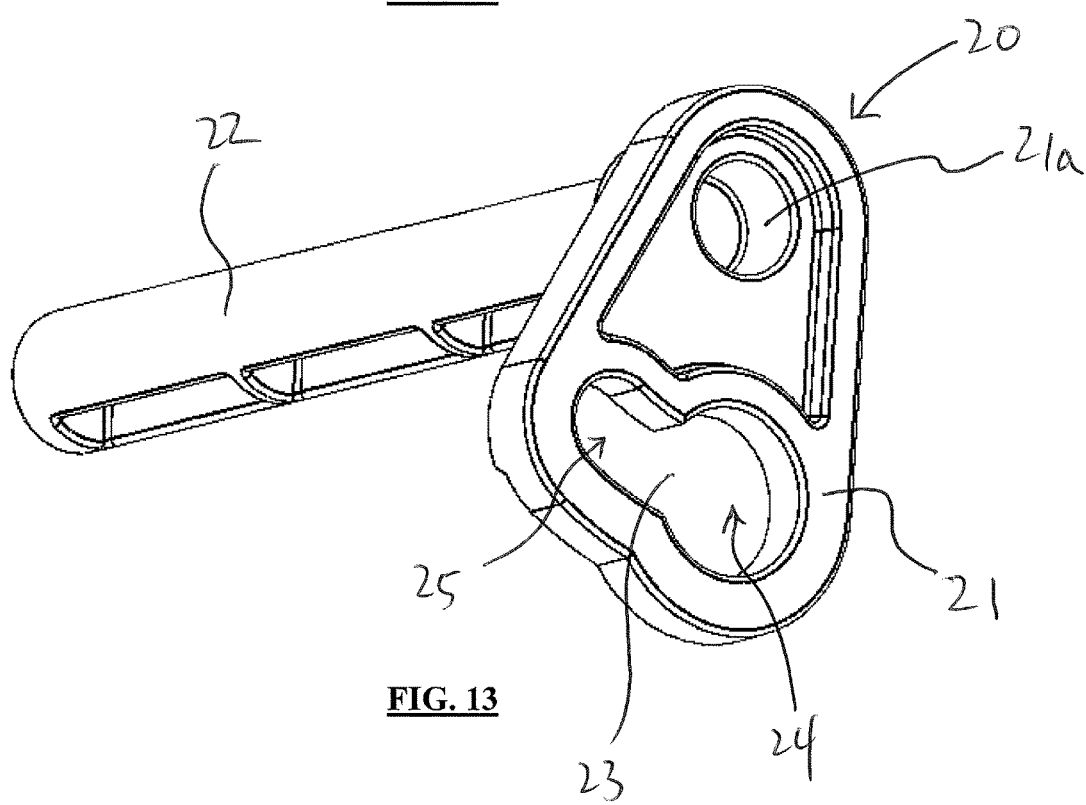
Figure 14:
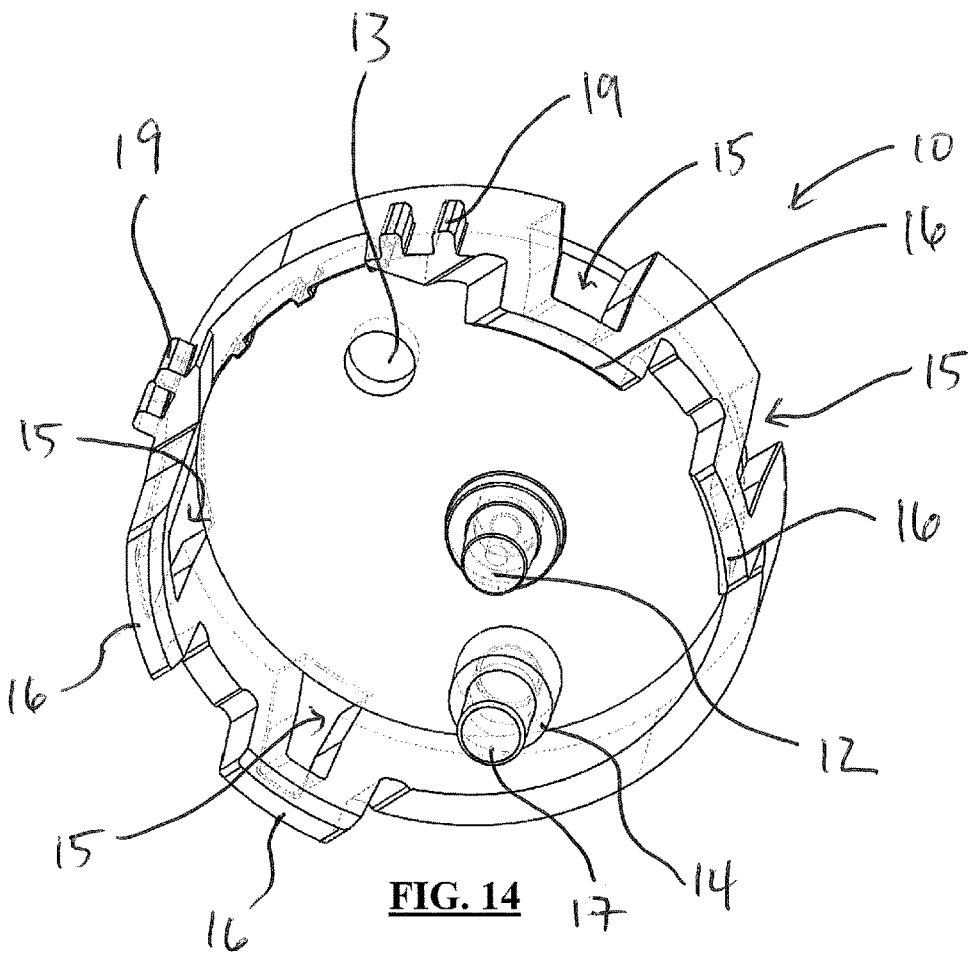
FIGS. 14 and 15 are perspective distal and proximal views, respectively, of a rear cover assembly of the screw cartridge shown in FIG. 1A.
Figure 15:
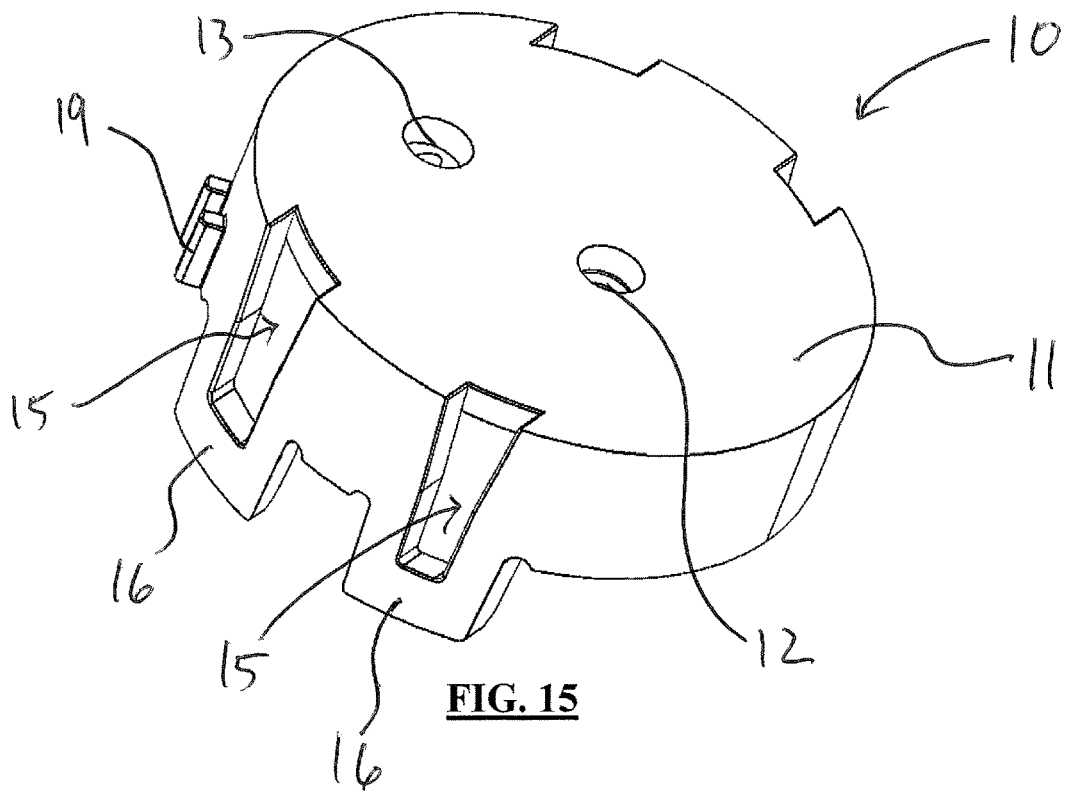

As shown in FIGS. 12 and 13, blade lock 20 has a proximal flange 21 and a distal shaft 22. Flange 21 is generally triangular and has a key-hole shaped aperture 23 of which a first portion 24 has a first maximum diameter and a second portion 25 has a second maximum diameter that is smaller than that of first portion 24. First and second portions 24, 25 need not be completely circular, but include different maximum diameters as described. For instance, second portion 25 includes a short slot and a circular end. Shaft 22 of blade lock 20 includes a cam groove 26 that has a V-shaped profile. Cam groove 26 has a first section 27 that extends longitudinally along a first axis parallel to that of shaft 22, a second section 28 that extends longitudinally along a different second axis that is also parallel to that of shaft 22, and a transition section 29 that diagonally or helically bridges first and second sections 27, 28. A cross-section of shaft 22 as defined by cam groove 26 is evidenced by the configuration of distal face 22a of shaft 22, shown in FIG. 12. Distal face 22a is generally circular except for the presence of a V-shaped notch defined by cam groove 26. This cross-section is the same along the axis of shaft 22 based on the location of cam groove 26. The profile of distal face 22a substantially matches that of noncircular aperture 64 of extension housing 60. Thus, when blade lock 20 is disposed within noncircular aperture 64 of extension housing 60, the orientation of blade lock 20 with respect to extension housing 60 will be dictated by the depth to which blade lock 20 is inserted, which is facilitated by the interaction of noncircular aperture 64 with cam groove 26 of shaft 22.

Outer housing 50 is shown in FIGS. 1A, 1B, 7, and 8 and includes a cylindrical sidewall 51 and a proximal end wall 52, which defines apertures 53a-c. Aperture 53a, while not threaded itself, accommodates threaded shaft 42 of extension screw 40 and shaft 37 of blade 30. Aperture 53b is configured for distal shaft 22 of blade lock 20 to extend and rotate therethrough. Aperture 53c is sized for boss 65 and extension housing magnet 66 to extend distally through proximal end wall 52 to interact with driver 300 as described above. A recess 53d is positioned to receive a rear cap magnet 17 of rear cover assembly 10, as described below. Recess 53d is not a full aperture through proximal end wall 52, but is a recess for spacing of rear cap magnet 17 between outer housing 50 and rear cover assembly 10. Ribs 54 extend inwardly from cylindrical sidewall 51 and are spaced accordingly to interface with grooves 67 on the outer face of sidewall 61 of extension housing 60. In this way, when extension housing 60 is moved along its longitudinal axis, it maintains its rotational orientation with respect to outer housing 50 so that extension housing 60 can translate and not rotate with respect to outer housing 50. The contour of an arrow 55 is provided on an outer surface of cylindrical sidewall 51 to instruct the user as to the direction of insertion of outer housing 50 into driver 300. Tabs 56 are disposed within recesses 57 on the outer surface of cylindrical sidewall 51 and mate with rear cover assembly 10, as discussed below.

As shown in FIGS. 1A, 1B, 14, and 15, rear cover assembly 10 fits over proximal end wall 52 of outer housing 50. An aperture 13 in a proximal end wall 11 of rear cover assembly 10 allows proximal end 31 of driver blade 30 to extend therethrough so that proximal end 31 can be actuated by driver 300. A protrusion 12 of rear cover assembly 10 mates with a depression 21a in blade lock 20 to keep blade lock 20 aligned when it is rotated about its axis. A boss 14 accommodates rear cap magnet 17, which communicates with a digital hall sensor disposed on the sensor board within driver 300 that receives information about the presence/absence of cartridge 100 by detecting rear cap magnet 17. The digital hall sensor is either on or off and outputs a corresponding voltage. Extensions 16 each project distally from proximal end wall 11 around an outer circumference thereof. Each extension 16 defines a window 15 and is configured to extend within recesses 57 of outer housing so that tabs 56 mate with windows 15 to removably secure rear cover assembly 10 to outer housing 50. Pairs of external ribs 19 on the outer housing 10 accommodate insertion into driver 300 to prevent a user from inserting outer housing 10 into driver 300 the wrong way.

Screw magazine assembly 200 and its components are shown in FIGS. 1A-1C and 16-26 and include a screw lid 210, an indexing spring 220, a plurality of screws 230 or other implants, a screw carrier 240, a rotor 250, and a screw magazine base 260. Screw magazine assembly 200 can be loaded into a distal end of extension housing 60 to be manipulated by other components of screw cartridge 100 to facilitate automatic loading and insertion of screws 230 via driver blade 30. Prior to the utilization of the device, the primary functions of the screw magazine assembly 200 are at least to (1) house and protect the components of screw magazine assembly 200, particularly blade 30 and screws 230, during shipping and use; (2) allow the components to be sterilized with Ethylene Oxide (EtO) and remain sterile due to the design and open sections of screw magazine assembly 200; and (3) protect the user from blade 30 and screws 230, and protect all elements during the shipping and initial loading of screw magazine assembly 200 into driver 300.

Screw magazine base 260 is shown in FIGS. 1A-C, 16A-C, and 26 and has a floor 261 and a cylindrical sidewall 262 extending upward therefrom. A split boss 263 also extends upward from floor 261 within cylindrical sidewall 262. An aperture 264 is defined by floor 261 and provides a passage through which screws 230 can exit screw magazine assembly 200. Two groups of snap features 265, 266 are disposed on an outer surface of cylindrical sidewall 262 and are positioned to engage openings 69 in sidewall 61 of extension housing 60 to lock screw magazine assembly 200 into extension housing 60 during use of cartridge 100. One group of snap features 266 has three features to distinguish it from the other group. Snap features 266 are different sizes such that they can differentiate the orientation of screw magazine base 260. Four individual extensions 267 are for alignment with voids in sidewall 61 at the end of grooves 67 of extension housing 60. Screw magazine base 260 can be formed of a transparent or translucent material to allow a user to see how many screws 230 are within screw magazine assembly 200 and the locations of same.

Figure 22:
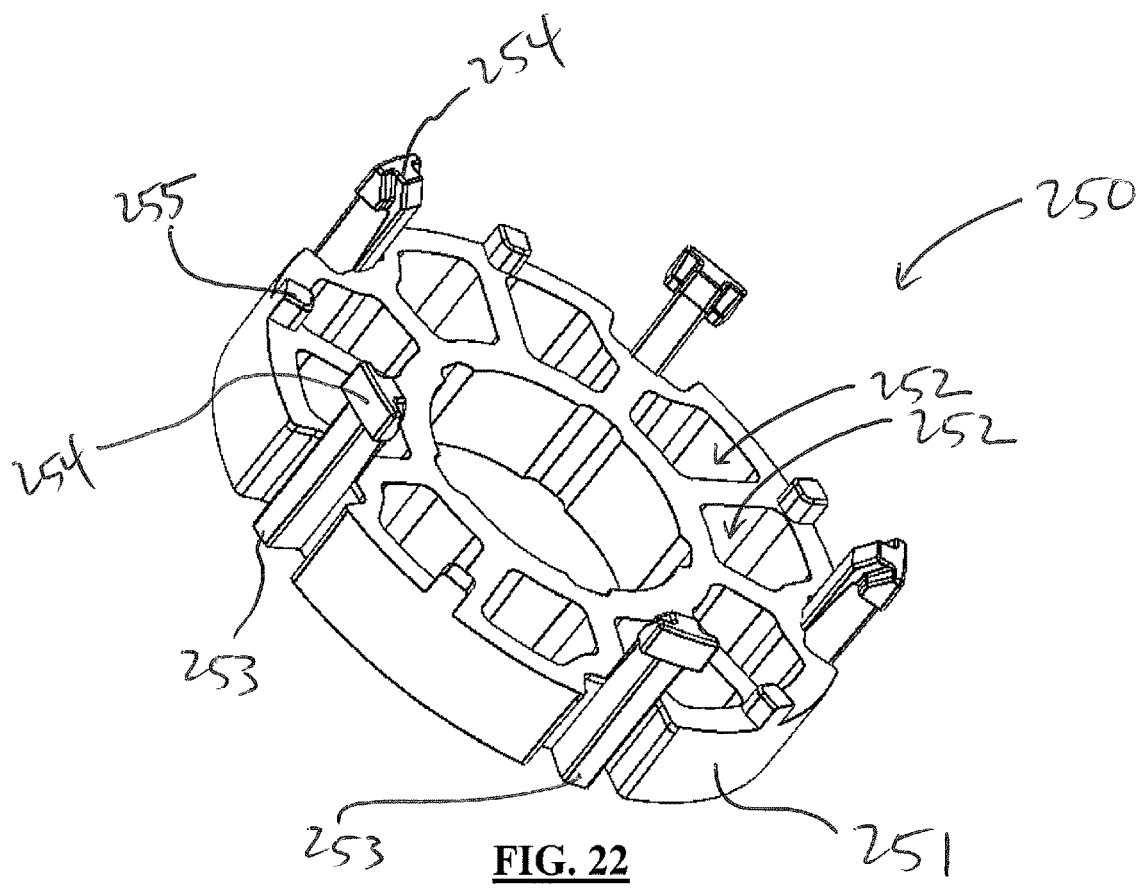
FIGS. 22 and 23 are perspective proximal and distal views, respectively, of a rotor of the screw magazine assembly shown in FIG. 16A.
Figure 23:
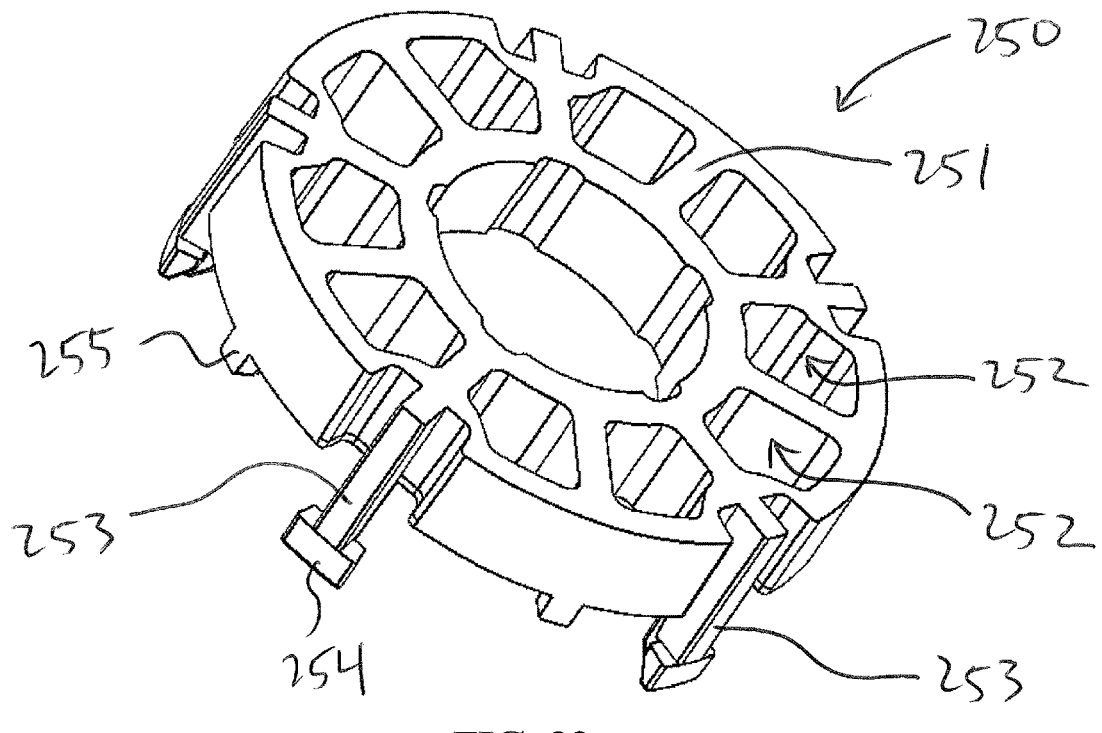

As shown in FIGS. 22 and 23, rotor 250 has an annular body 251 defining a plurality of passages 252 through which screws 230 are passed, respectively. Around an outer circumference of annular body 251, flanges 253 and posts 255 extend upward to a height above annular body 251. Each flange 253 has an enlarged head 254 at an upper end thereof. Flanges 253 and posts 255 are used for connection and rotational stability with other elements of screw magazine assembly 200, as described further below.

Figure 17:
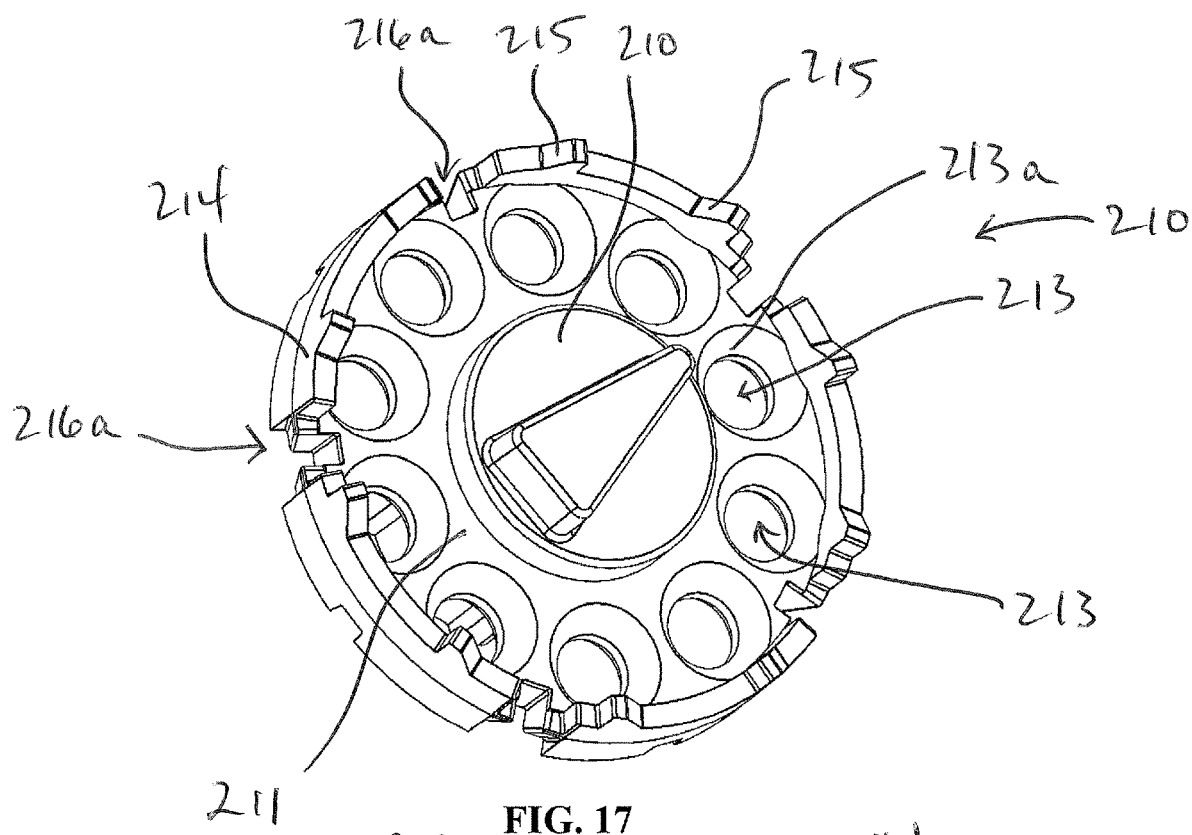
FIGS. 17 and 18 are perspective proximal and distal views, respectively, of a screw lid of the screw magazine assembly shown in FIG. 16A.
Figure 18:
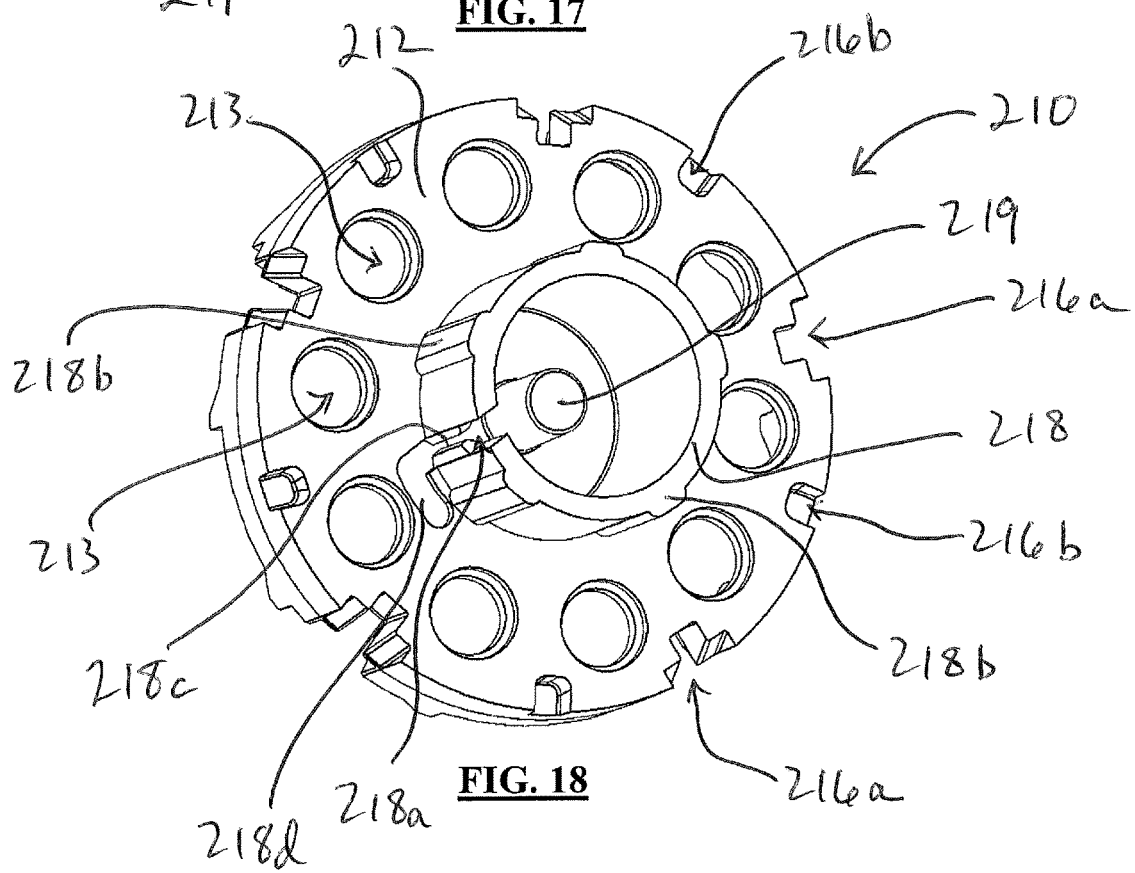

Screw lid 210 is shown in FIGS. 17 and 18 having an upper side 211 and a lower side 212, with a plurality of screw holes 213 extending therebetween. Each screw hole 213 includes a chamfered proximal circumference 213a to provide a funnel surface to guide driver blade 30 toward head 231 of screw 230 seated within screw hole 213. An annular flange 214 extends around screw lid 210 and has triangularly-shaped protrusions 215 extending upwardly from upper side 211. Protrusions 215 are positioned to interact with ribs 68 of extension housing 60 to facilitate indexing of screw magazine assembly 200, as explained further below. Notches 216a and 216b are spaced circumferentially around annular flange 214. Notches 216a are configured to mate and engage with flanges 253 and their enlarged heads 254 of rotor 250 to rotationally secure screw lid 210 and rotor 250 together, while notches 216b are configured to house posts 255 of rotor 250 to further rotationally lock screw lid 210 to rotor 250 in their connected configuration. A triangular platform 217 extends upwardly from upper side 211 and provides an indication of rotational orientation to the user. From lower side 212, a boss 218 having a slot 218a and external ribs 218b extends around a pillar 219 for mating and orienting spring 220. Within slot 218a, two ribs 218c face each other to create a narrower width than the width of slot 218a defined solely by the edges of boss 218. A recess 218d is disposed in lower side 212 extending from the base of slot 218.

As shown in FIGS. 21A-G, screw carrier 240 is a thin, flat, monolithic piece of material defining an outer perimeter 241 and a central aperture 242 with an inner perimeter 243. Outer perimeter 241 includes circumferentially spaced notches 244 and 245 configured to accommodate flanges 253 of rotor 250 and posts 255 of rotor 250, respectively. Notches 246 on inner perimeter 243 are contoured to accommodate external ribs 218b of screw lid 210. Prior to utilization of the device, the primary function of screw carrier 240 is to hold screws 230 during transport/storage and help retain them in the correct position/alignment for eventual loading of screws 230 onto blade 30. A plurality of screw-holding apertures 247 are spaced around screw carrier 240 and each include three fins or lobes 248 to releasably retain a screw 230, which can be a 1.5×4 mm screw or any other screw. Of course, it is not necessary that each aperture 247 of screw carrier 240 be loaded with a screw 230 for screw carrier 240 to be used. Each screw 230 of the plurality can be disposed within an aperture 247 of the plurality of apertures so that each screw 230 sits within a single aperture 247, whether or not all apertures 247 are filled.

Figure 27A:
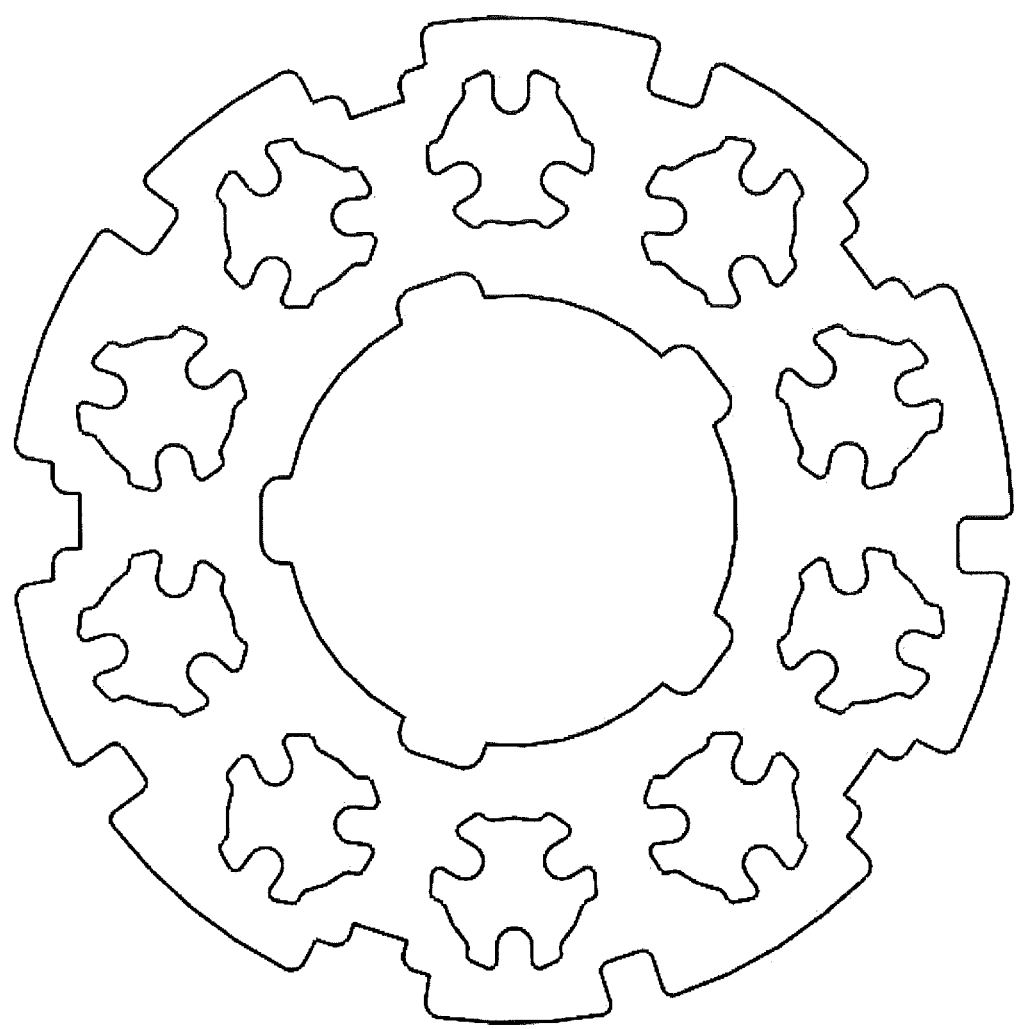
FIGS. 27A and 27B are top and front views, respectively, of a screw carrier in accordance with another embodiment of the present invention.
Figure 27B:
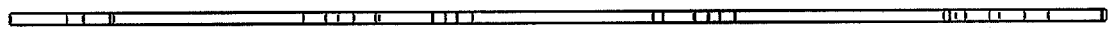

The number of screw-holding apertures 247 within screw carrier 240 can be eight, ten, twelve, or any other number according to size and need. The thin nature of screw carrier 240 dictates that lobes 248 are malleable, deformable, and/or flexible to hold a screw 230 in a substantially fixed position, while allowing the screw 230 to push through the irregularly shaped aperture 247 by flexing or bending lobes 248 during passage, as described further below. Lobes 248 are designed in material, thickness, and shape to hold screws 230 with a particular amount of retaining force such that blade 30 can mate with each screw 230 and generate retention force, which allows the blade 30 and screw 230 to eventually press through lobes 248 and remain attached together. Upon a predetermined force applied by blade 30 to screw 230, screw 230 is disengaged from lobes 248 of screw carrier 240. Another embodiment of a screw carrier is shown in FIGS. 27A and 27B and includes differently sized and shaped lobes for engagement with screws 230.

Figure 16A:
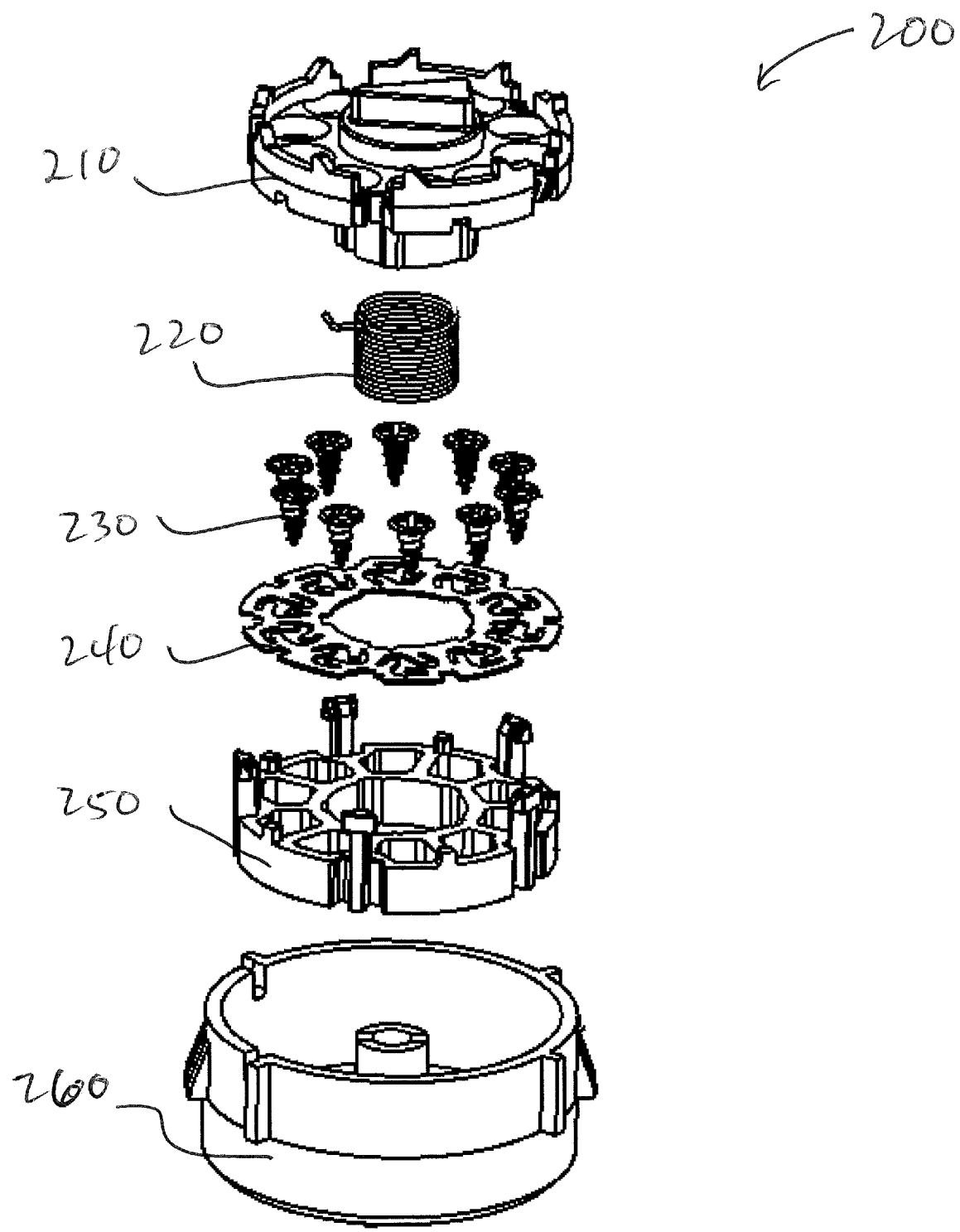
FIG. 16A-C are perspective exploded, perspective proximal assembly, and distal assembly views, respectively, of a screw magazine assembly of the screw cartridge shown in FIG. 1A.
Figure 16B:
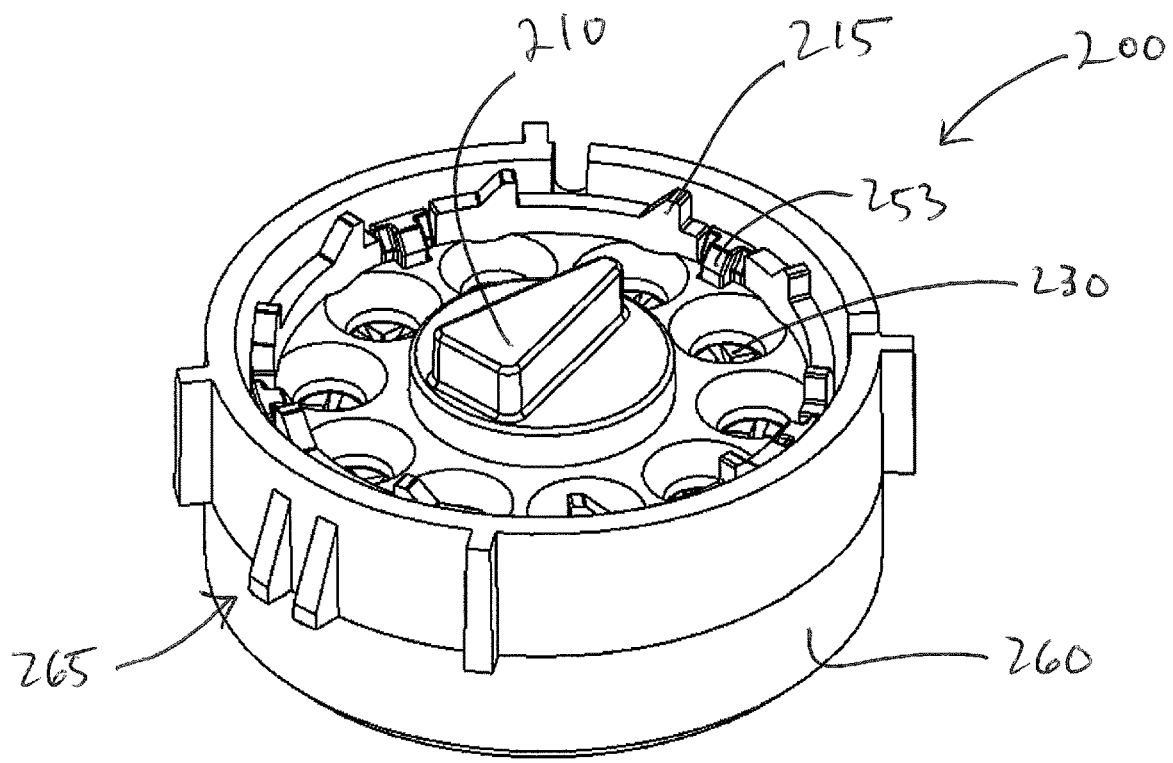
Figure 16C:
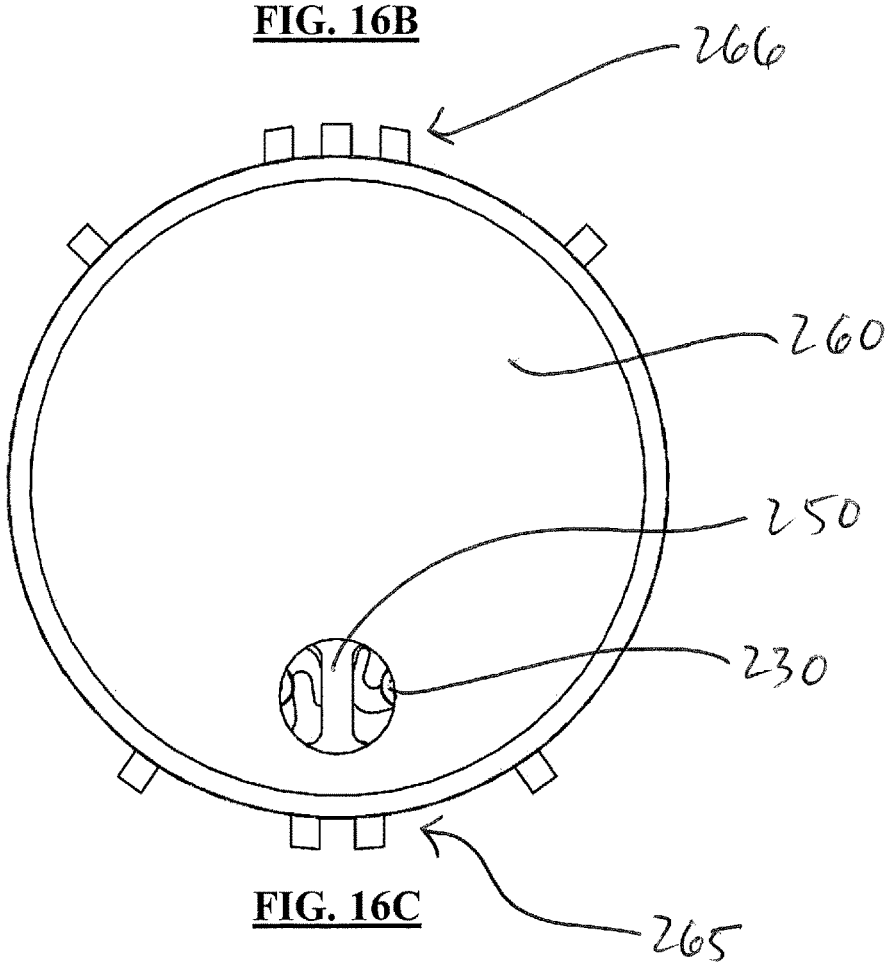
Figure 19:
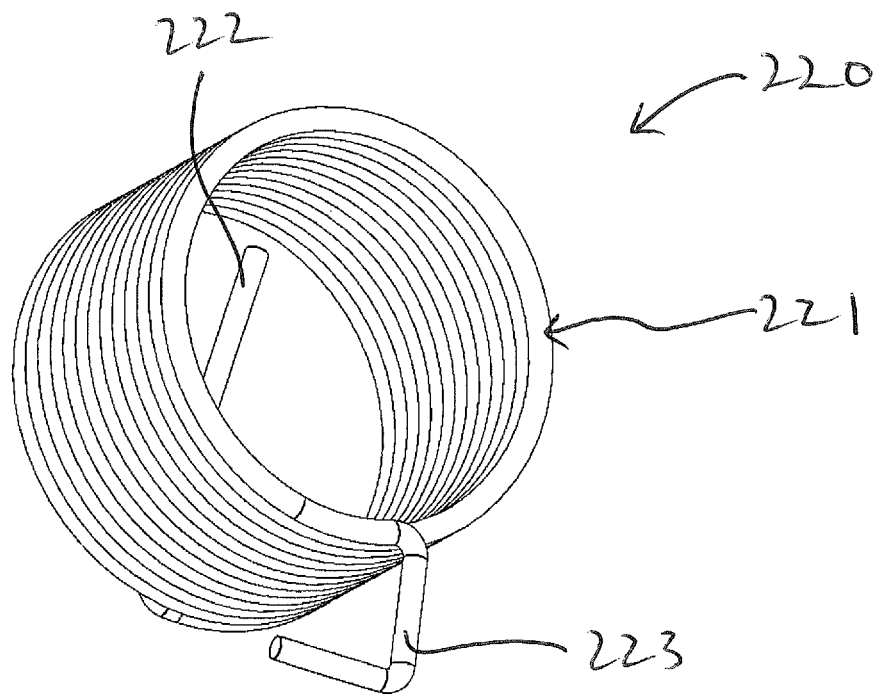
FIG. 19 is a perspective distal view of an indexing spring of the screw magazine assembly shown in FIG. 16A.
Figure 20:
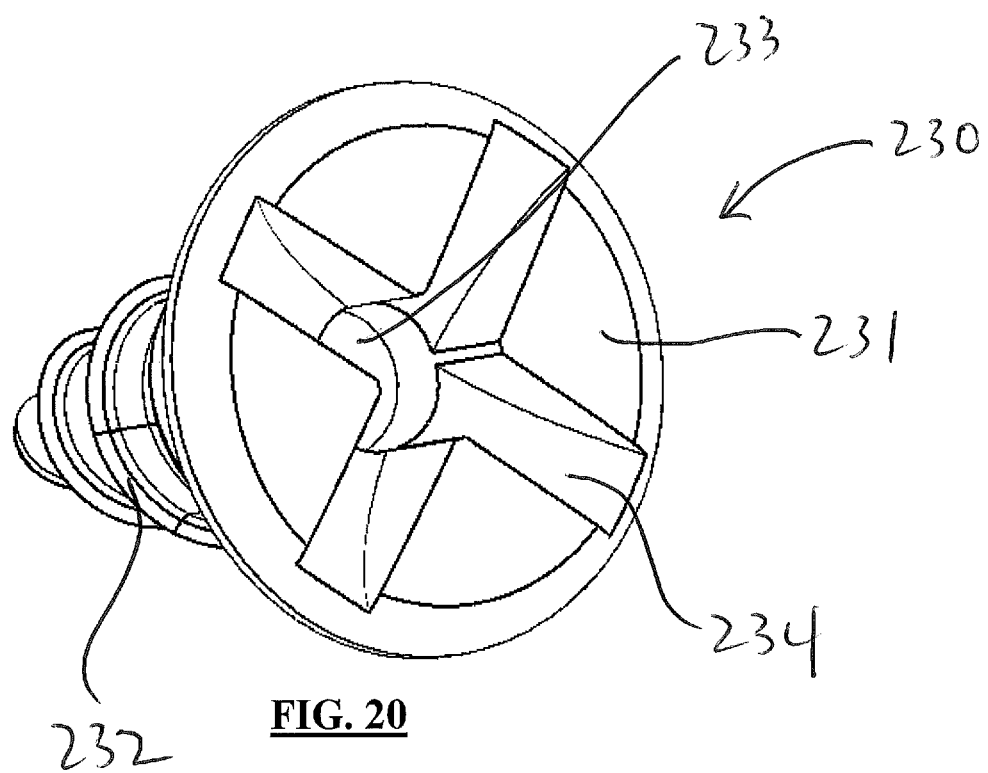
FIG. 20 is a perspective proximal view of a screw of the screw magazine assembly shown in FIG. 16A.
Figure 21A:
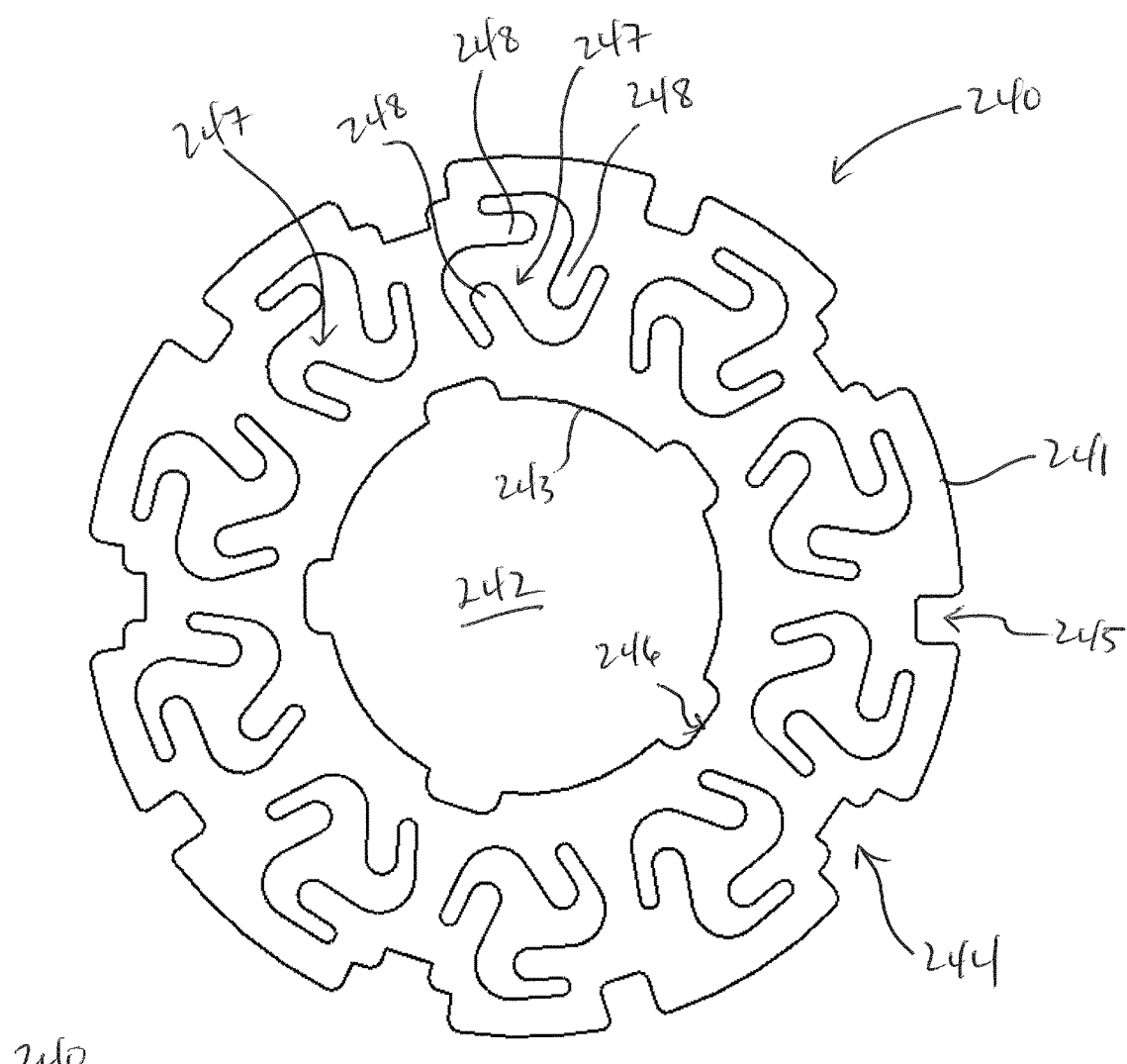
FIGS. 21A-G are top, front, back, bottom, left, right, and perspective top views, respectively, of a screw carrier of the screw magazine assembly shown in FIG. 16A.
Figure 21B:
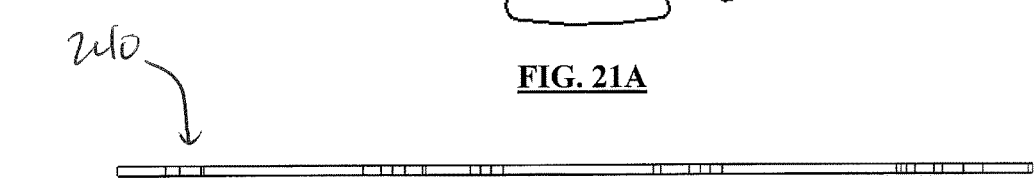
Figure 21C:
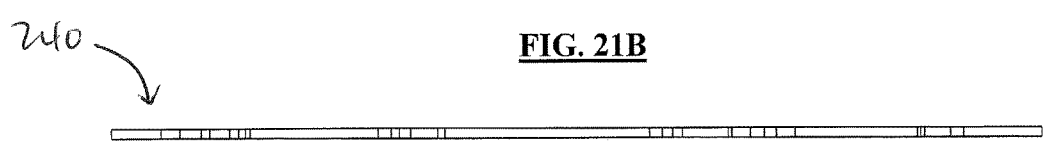
Figure 21D:
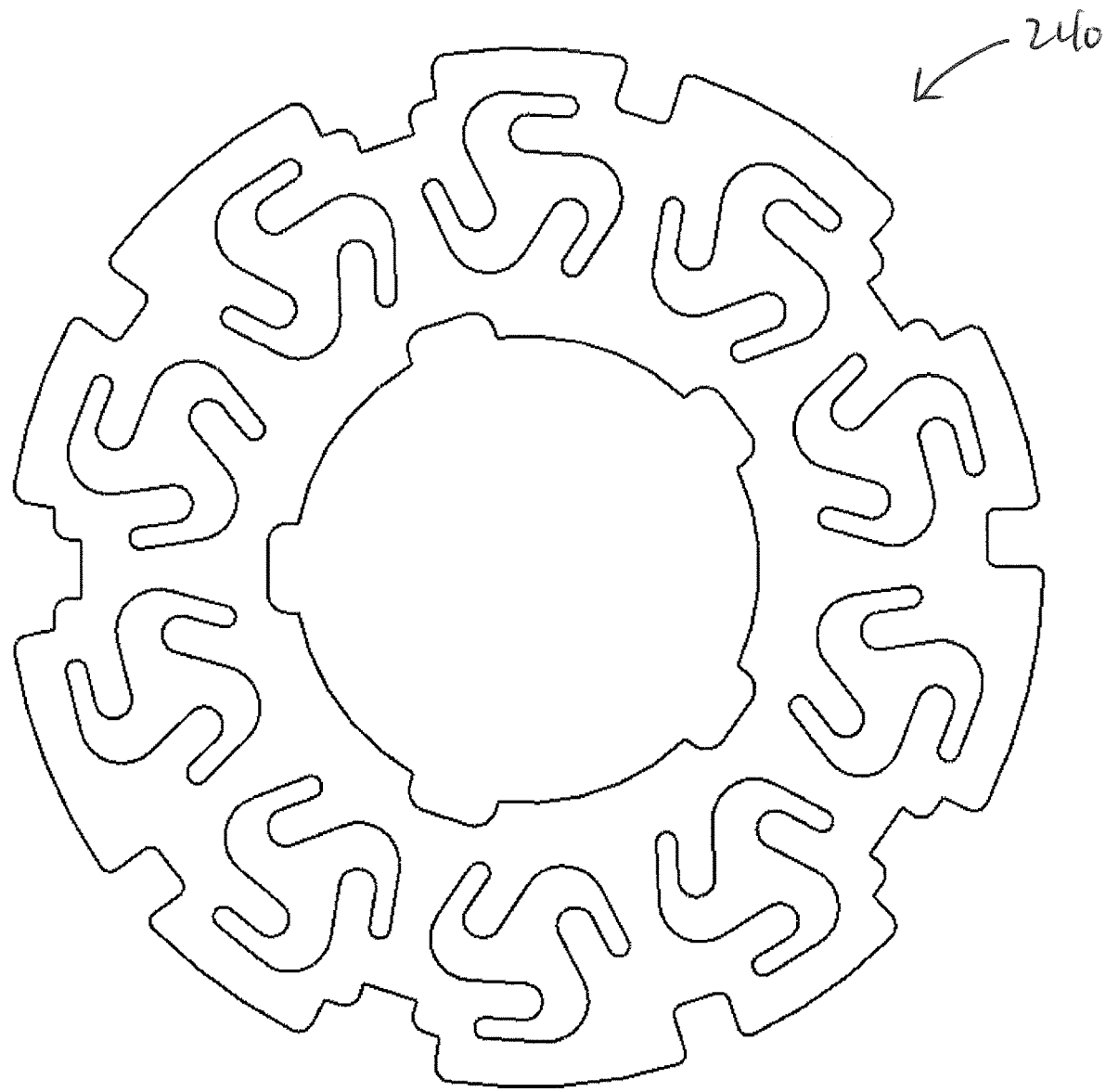
Figure 21E:
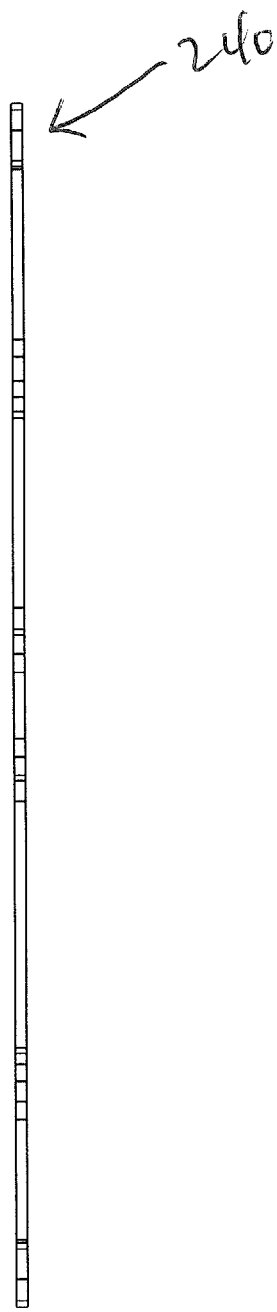
Figure 21F:
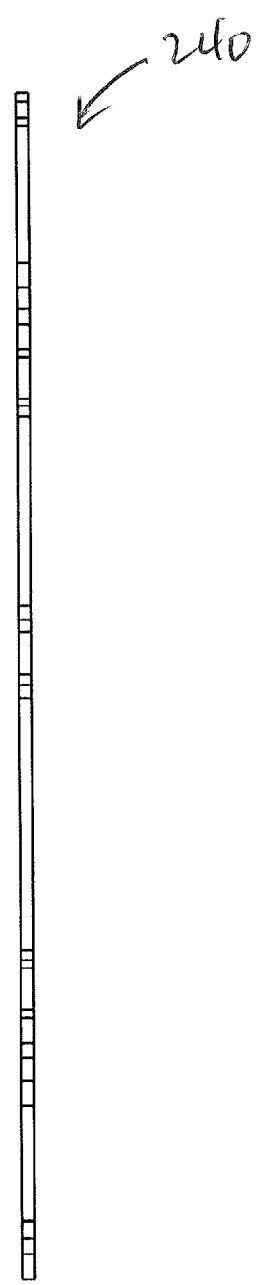
Figure 21G:
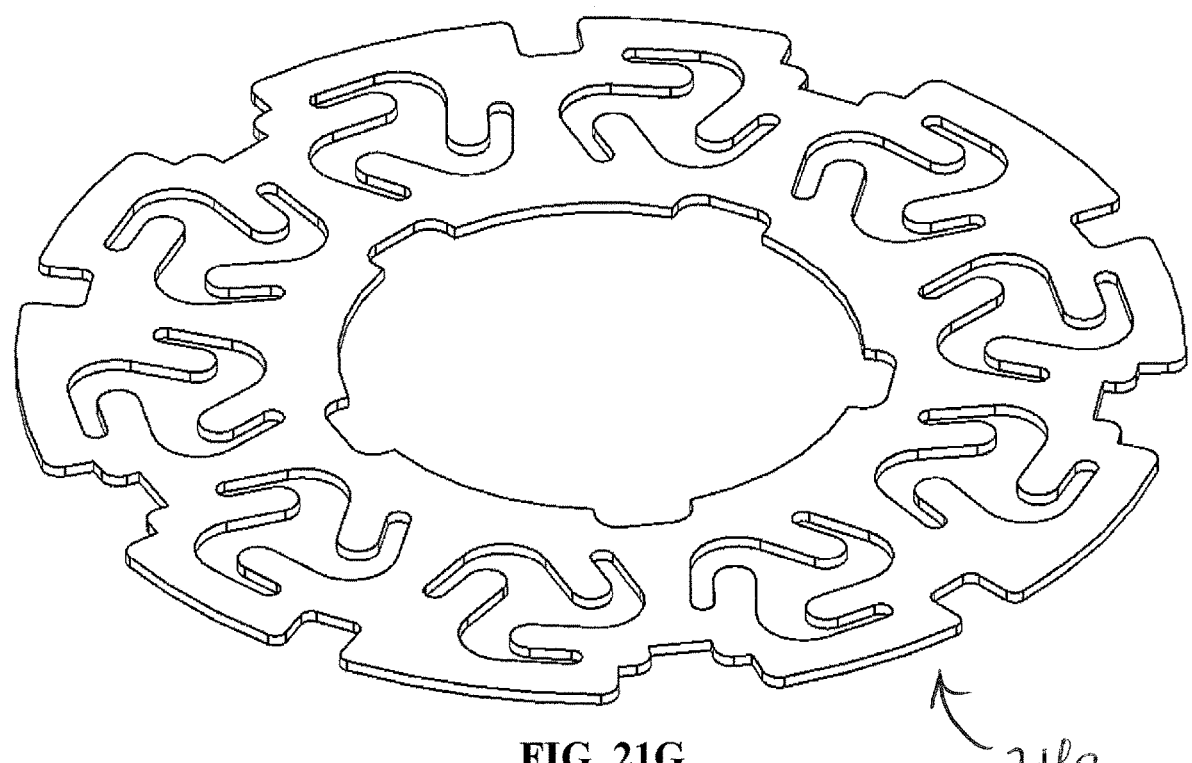
Figure 24:
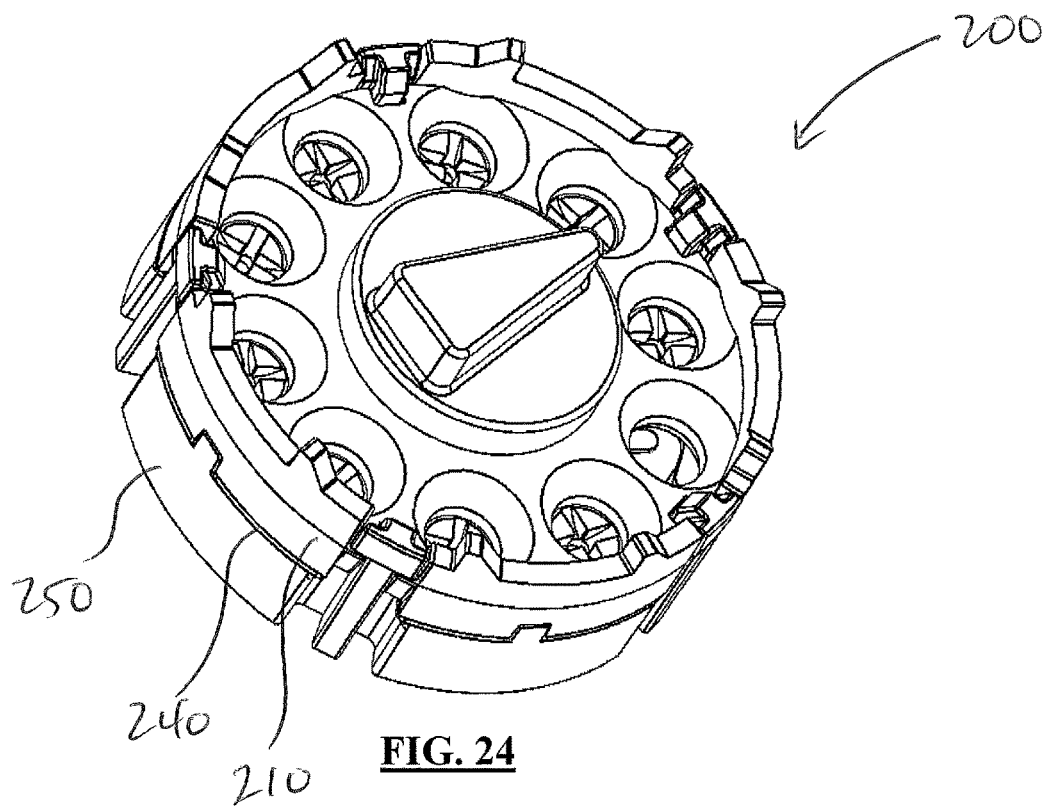
FIGS. 24 and 25 are perspective proximal and distal assembly views, respectively, of the screw lid, the indexing spring, the screw carrier, the rotor, and several screws of the screw magazine assembly shown in FIG. 16A.
Figure 25:
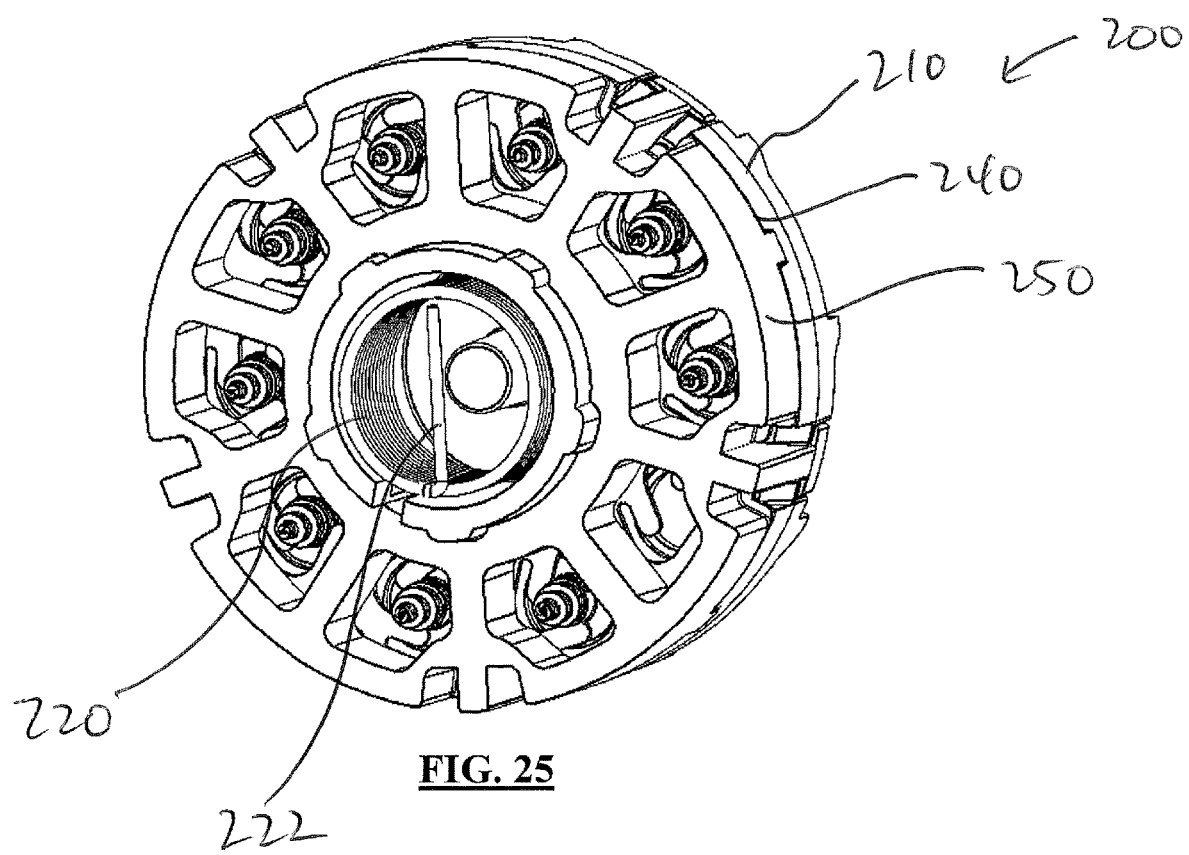
Figure 26:
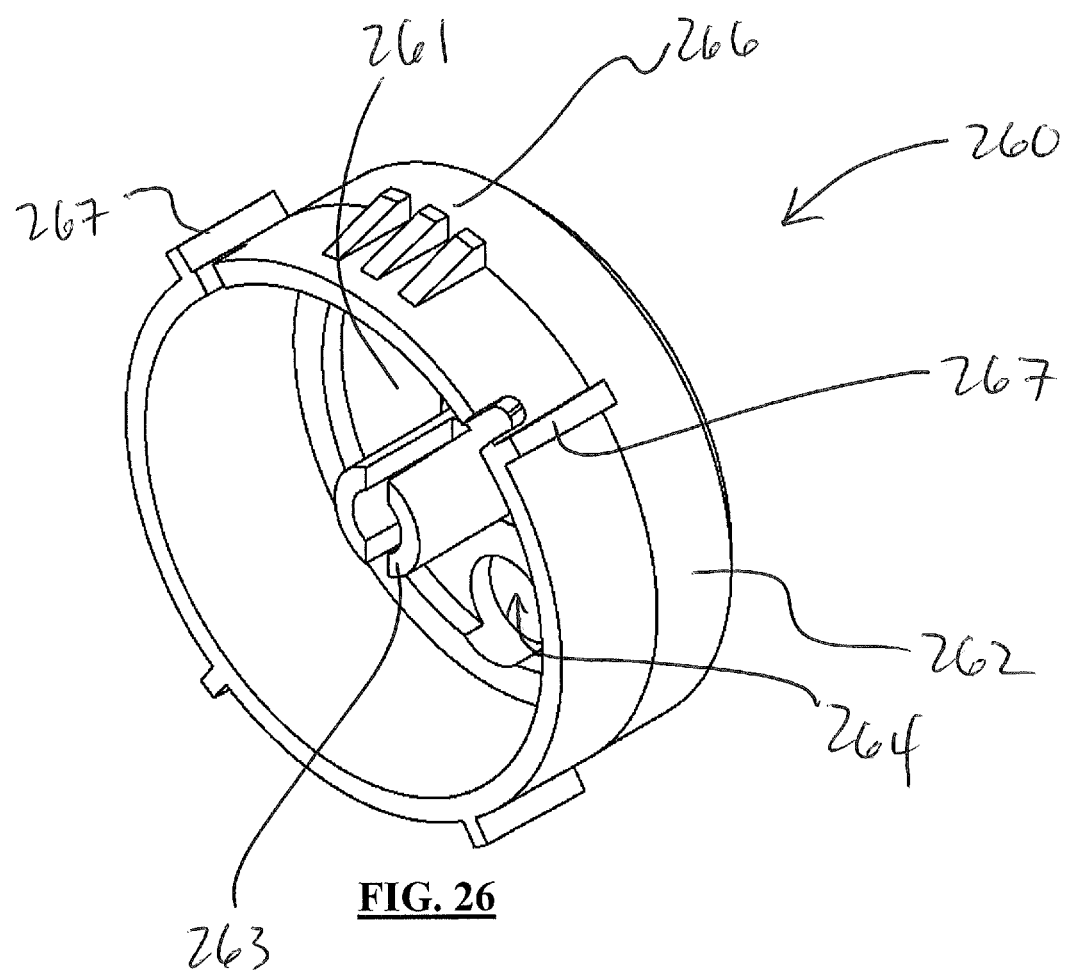
FIG. 26 is a perspective proximal view of a screw magazine base of the screw magazine assembly shown in FIG. 16A.

The exploded view of screw magazine assembly 200 depicted in FIG. 16A shows that screw carrier 240 is sandwiched between rotor 250 and screw lid 210, which are secured together via flanges 253. This is also depicted in FIGS. 24 and 25 in which rotor 250 and screw lid 210 are assembled around screw carrier 240. An indexing spring 220, shown in FIGS. 16A, 19, and 25, is configured as a coil 221 and has a first end 222 extending toward a center of the coil 221 and a second end 223 projecting outward from the coil 221. Second end 223 extends generally normal from the circumference of the coil 221 and further so that it forms an angle that is about ninety degrees. First end 222 of indexing spring 220 can be seen in FIG. 25 within boss 218 of screw lid 210. Spring 220 sits within boss 218 of screw lid 210, such that second end 223 extends between ribs 218c and within slot 218a with the right-angled contour of second end 223 disposed at least partially within recess 218d and outside of boss 218. In this way, spring 220 can be prewound to cause screw lid 210 and the other components rotationally locked to screw lid 210 to rotate to provide the ability of screw magazine assembly 200 to rotate within screw cartridge 100 during indexing of screws 230 when cartridge is in use. During assembly, indexing spring 220 is wound and stays wound until the product is used. This spring force is what allows the indexing of screws.

Each screw 230, depicted in FIGS. 16A, 16B, 20, and 25, includes a head 231 and a threaded shaft 232. Head 231 is configured to engage with distal end 35 of blade 30. A cavity 233 is centered with respect to an X-shaped recess 234 that mates with the Philips-head configuration of distal end 35.

Once screw lid 210 and rotor 250 are connected to sandwich indexing spring 220 and screw carrier 240, which holds a screw 230 in each aperture 240, the assembly is placed into screw magazine base 260 to form screw magazine assembly 200. Screw magazine assembly 200 can then be loaded into a distal end of extension housing 60 so that it is seated on the distal ends of ribs 68.

Twist lock 70, which is depicted in FIGS. 1A-1C, 5, and 6, includes a proximal edge 71, a cylindrical wall 72, and a distal rim 73. Extending inward from cylindrical wall 72 are two tabs 74 that engage circumferential windows 58 of outer housing 50 when twist lock 70 is engaged with outer housing. In this way and because the circumferential windows 58 extend around portions of the outer circumference of cylindrical sidewall 51, twist lock 70 can maintain its connection with outer housing 50 while being able to rotate to some extent with respect to outer housing 50. Twist lock 70 also includes two flanges 75, each having an outward facing knob 76, which allows twist lock 70 to lock cartridge 100 into driver 300. The small protruding circles of flanges 75 fit into corresponding circles on driver 300.

A method of using a surgical screwdriver includes first placing screw magazine assembly 200 with its screws 230 into the distal end of screw cartridge 100. Screw cartridge 100 loaded within the cavity of driver 300, after which screw cartridge 100 can be secured with twist lock 70. Preferably when it is initially loaded, screw cartridge 100 is configured with extension housing 60 extended distally and blade lock 20 in its locked position with respect to blade 30. Thus, each of screw-holding apertures 247 can be filled with a screw 230 so that screw cartridge 100 is at maximum capacity.

When a trigger 301 on driver 300 is depressed, a motor of driver 300 operates an internal mechanism of driver 300 to engage noncircular end 34 of blade 30, which rotates shaft 30 in a right-hand rule or clockwise direction. This also rotates extension screw 40 since collar 32 of blade 30 is disposed within recess 44 of extension screw 40, and since blade lock 20 locks blade 30 in that position. During this movement, extension screw 40 moves extension housing 60 proximally, which also eventually moves blade lock 20 from its locked to its unlocked position due to cam groove 26 interacting with noncircular aperture 64 of extension housing 60. Cam groove 26 is particularly configured so that the movement of extension housing dictates the time at which blade lock 20 is oriented into the unlocked position.

As blade 30 spins and moves distally within extension housing 60, which turns extension screw 40, which thus retracts extension housing 60 around blade 30, it comes into contact with the chamfered proximal circumference 213a of a screw hole 213 of screw lid 210. Further distal movement of blade 30 within extension housing 60 does two things. First, it funnels or centers the distal end of blade 30 within screw hole 213 by rotating screw lid 210 slightly within screw magazine base 260, thus allowing blade 30 to contact and engage screw 230 so that it can be passed through aperture 264 in floor 261 of base 260, with which it is also aligned. Second, the movement of extension housing 60 allows blade 30 to place pressure on screw lid 210 to tip or tilt that circumferential side of screw lid 210 distally so that the protrusions 215 that are currently engaged with ribs 68 of extension housing 60 become disengaged therefrom. Initially, a central axis of screw hole 213 and a central axis of blade 30 are slightly offset and not exactly collinear, which facilitates this interaction between blade 30 and screw lid 210 as explained above to create the indexing ability of screw cartridge 100.

When blade 30 engages screw 230, protrusion 36 of blade 30 centers itself into cavity 233 of head 231 of screw 230. Screws 230 are designed such that the wings of the tip of driver blade 30 press into and slightly deform screw head 231, which is made of a relatively softer material, to create retention force, such that blade 30 can temporarily retain screw 230 more easily and to ensure that screw 230 does not fall off blade 30 during use before it contacts the intended medium. The tip of blade 30 is pressed into the head of screw 230 by the action of extension housing 60 being retracted in order to initiate mating. The rotation blade 30 at a particular speed, along with screw carrier 240 holding screw 230 in place, extension housing 60 retracting at a particular speed, and the centering of blade 30 using the chamfers, allows the wings of blade 30 to line up with the corresponding wings on the screw head 231 during the mating process.

Screw carrier 240 is strong enough to resist the force of blade 30 during the beginning of extension housing 60 retracting, allowing screw 230 to stay in the same x-axis position while the spinning blade tip presses into the screw head. Screw carrier 240 in this step provides enough of a counteracting force such that screw 230 is firmly pressed onto the wings of blade 30, causing deformation of the head of screw 230 around blade 30 and thereby generating the screw retention force between screw 230 and blade 30. This process generates higher, more consistent retention force between screw 230 and blade 30 than a similar process executed by a manual mating of a screwdriver head and a blade.

In the final stage of mating, screw carrier 240 deforms to allow screw 230 and blade 30 to pass through to the other side of screw magazine assembly 200 and present the functional assembly of the mated screw 230 and blade 30 to the user for insertion. This process moves head 231 of screw 230 to deflect lobes 248 of screw-holding aperture 247 to free screw 230 from screw carrier 240. The plastic deformation of lobes 248 allows blade 30 to spin during the insertion of screw 230 and allows blade 30 to retract through back into screw cartridge 100 during the next loading phase. As extension housing 60 continues to retract to its fully retracted position, the wings eventually give way allowing screw 230 and blade 30 to pass through screw hole 213 in screw lid 210 and the hole in rotor 252.

While blade 30 is within screw hole 213 at this point preventing any further rotation of screw lid 210 about split boss 263 of base 260, the protrusions 215 are effectively moved past ribs 68 they previously contacted due to the slight movement of screw lid 210 during the centering of blade 30 within screw hole 213. Thus, when blade 30 is eventually moved proximally out of screw hole 213, screw lid 210 is rotated under the influence of indexing spring 220 to index screw lid 210 until the protrusions 215 contact subsequent ribs 68 to maintain this new rotational position until the next adjacent screw 230 can be loaded onto blade 30 in the same way as described above. Extension housing 60 includes two ribs 68 in proper locations with respect to protrusions 215 for this purpose, and a third rib 68 in a generally opposite orientation around cylindrical sidewall 61 to prevent screw lid 210 from being tipped too far and inadvertently rotating beyond what is intended to properly index springs 230 one by one. During this part of the process, since blade lock 20 is in its unlocked position when extension housing 60 is fully retracted, this allows blade 30 to back out of outer housing 50 slightly upon the user applying pressure to blade 30 and screw 230 into the target substrate so that it can disengage from extension screw 40 and rotate freely in order to rotate and insert screw 230 into a medium.

After insertion of screw 230, the user removes the pressure off of the blade 30 and screw 230 against the target, and the spring within the driver 300 returns collar 32 of blade 30 to engage with recess 44 of extension screw 40. This engagement and the counter-clockwise left-hand rule rotation of the motor within driver 300 moves extension housing 60 distally and eventually moves blade lock 20 from its unlocked to its locked position. Once blade 30 is moved proximally out of screw hole 213, as described above, indexing of screw lid 210 occurs. Triangular platform 217 on screw lid 210 is an arrow provided for assembly to give a reference point on where the first screw should be placed and how many rotations have been completed during winding. It is not visible to the user after assembly.

Indexing spring 220 can be loaded to the extent that it continuously applies pressure on screw lid 210 through the entire procedure of indexing all screws 230 located therein. In that way, spring 220 does not have to be set each time screw lid 210 is rotated and a screw 230 is inserted. Spring 220 is wound to allow for at least one complete revolution of screw lid 210, which is of course enough to empty all screws 230 during a procedure. To check how many screws remain in the middle of a procedure, a user can simply view the remaining screws through the transparent or translucent material of screw magazine base 260.

During this entire process, the driver can monitor and react to the state of the cartridge and the insertion procedure. Using its two hall sensors, driver 300 can perform state detection. The first relevant state is the "idle" state. This is when the digital hall sensor detects a digital voltage, which communicates an absence of a cartridge. The analog hall sensor detects a specific analog voltage in this positioning. In this state, if the activation button or trigger 301 is pressed, driver 300 will spin in the counterclockwise direction in order to indicate to the user that driver 300 is functioning but there is no cartridge detected.

When a cartridge is inserted, the digital hall sensor detects a different digital voltage which communicates the presence of a cartridge. This sensor will remain at this voltage throughout the rest of the states until the cartridge is removed from driver 300. This is still the "idle" state until the button 301 is pressed.

When the button 301 is pressed for the first time, driver 300 enters "align" state. Within driver 300 there is a blade switch which indicates when blade 30 has disengaged with extension screw 40. When blade 30 is disengaged from extension screw 40, blade 30 is allowed to rotate freely in order to insert a screw 230. When blade 30 is engaged with extension screw 40, the spinning of blade 30 is used to extend and retract extension housing 60, which is used for mating. In this state, driver 300 evaluates that the blade switch isn't activated. If it is not activated, driver 300 goes into "retract" state.

Screw cartridge 100, when it is new, comes in an extended state, so the analog hall sensor will output an analog numerical value voltage which represents the strength of the magnetic field it is experiencing. When the voltage is a certain analog value, the driver software knows that extension housing 30 is in the extended state and will rotate blade 30 clockwise to retract extension housing 30. As extension housing 30 is retracting, the analog hall sensor continuously monitors the location. When the relevant magnet reaches a mark represented by a particular analog voltage from the hall sensor, the motor speed will slow. When the magnet reaches a second mark, which is again represented by a specific analog voltage, the motor will stop. This indicates that extension housing 30 is fully retracted.

Driver 300 is now in "position" state. When blade 30 is disengaged from extension screw 40, blade 30 is allowed to rotate freely in order to insert a screw 230. When it is disengaged, and button 301 is activated, cartridge 100 itself is ready to insert a screw 230. Driver 300 looks for both the activation of the blade switch and the press of the activation button 301. Driver then enters "insert" state. When the user presses activation button 301 to insert a screw 230, the algorithm in driver 300 controls the insertion. Secondarily, the analog hall sensor is also monitored by driver 300 in this state, and if blade 30 slips back into extension screw 40 and begins to retract extension housing 60, the motor will be stopped in order to prevent cartridge damage.

Driver 300 then enters "hold" state. Driver 300 looks for an activation button press and then enters the "realign" state. Driver 300 evaluates the voltage of the analog hall sensor to know where extension housing 60 is located based on the previous steps. In this state, driver 300 evaluates that the blade switch isn't activated. If it is not activated, driver 300 goes into "extend" state.

During the "extend" state, the number of counterclockwise rotations of blade 30 is counted to extend extension housing 60. The specific number of rotations can be chosen so that as extension housing 60 extends from cartridge 100 there is no longer contact between blade 30 and screw magazine assembly 200, freeing the screw carrier spring force to index to the next screw 230, as described above. When the correct number of rotations has been performed, the motor stops and reverses direction.

Like before, in the extended state, the analog hall sensor will output a numerical analog value voltage which represents the strength of the magnetic field it is experiencing. When the voltage is a certain value, the driver software senses that extension housing 60 is in the extended state and will rotate blade 30 clockwise to retract extension housing 60. As extension housing 60 is retracting, the analog hall sensor continuously monitors the location. When the relevant magnet reaches the first mark, the motor speed will slow. When the magnet reaches the second mark, the motor will stop. This indicates that extension housing 60 is fully retracted.

This process of "position", "insert", "hold", "realign", "extend", "retract", "position" will continue throughout the use of cartridge 100. When cartridge 100 is empty of screws 230, the user will remove cartridge 100, and the entire process will begin again. During this whole process, the indexing spring continues to exert force and does not have to be re-set for each insertion step.

The cartridge 100 and screw magazine assembly 200 described herein are individual versions of these modular features of the present device. Different cartridges and/or magazine assemblies can be interchanged and used with the driver (or another suitable driver) to facilitate many different types of uses of the present technology.

In other embodiments, the present implants/screws can be provided in an array of sizes and/or configurations to provide modularity are the screws 230 and the screw carrier 240. This can allow the present system to be used for insertion of other implants and in many surgical locations and sites, i.e. sternal applications, suture anchor insertion, Delta screws, etc.

The cartridge and magazine assembly can be reusable. The parts can be disassembled and reprocessed by cleaning, for example by autoclave, to sterilize the parts for assembly and use in a subsequent procedure. The same or differently sized screws/implants could be used in subsequent uses. If there are screws left in a cartridge/magazine assembly after a procedure such as a surgery, the whole cartridge could be reprocessed and sterilized and used in another case. Another option is to remove the remaining screws before reprocessing so that they can be used in another procedure as loose screws or can be added to another cartridge.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. An implant magazine for use with a driver, the implant magazine comprising:
a plurality of implants;
an implant carrier defining a plurality of apertures, each implant of the plurality of implants being disposed within an aperture of the plurality of apertures, wherein an implant is disengaged from the implant carrier upon application of a predetermined force applied to the implant;
a base defining a cavity in which the implant carrier and the plurality of implants are disposed; and
an indexing spring to rotate the implant carrier within the base, wherein the indexing spring is loaded to rotate the implant carrier about one complete revolution of the implant carrier so that each implant of the plurality of implants is disposed at different times adjacent an aperture in the base through which an implant can be passed.

2. The implant magazine of claim 1, wherein each aperture in the implant carrier is defined by one or more deformable fins configured to contact the implant.

3. The implant magazine of claim 1, wherein the plurality of implants is a plurality of screws.

4. A cartridge for use with a driver, the cartridge comprising:
an implant magazine comprising:
a plurality of implants;
an implant carrier defining a plurality of apertures, each implant of the plurality of implants being disposed within an aperture of the plurality of apertures, wherein an implant is disengaged from the implant carrier upon application of a predetermined force applied to the implant;
a base defining a cavity in which the implant carrier and the plurality of implants are disposed; and
an indexing spring to rotate the implant carrier within the base, wherein the indexing spring is loaded to rotate the implant carrier about one complete revolution of the implant carrier so that each implant of the plurality of implants is disposed at different times adjacent an aperture in the base through which an implant can be passed,
a housing in which the implant magazine is disposed; and
a blade having a longitudinal axis and being at least partially and rotatably disposed within the housing;
wherein the blade has a working configuration and a loading configuration, wherein in the working configuration, rotation of the blade causes rotation of an implant of the plurality of implants and does not move the housing along the longitudinal axis of the blade, and wherein in the loading configuration, rotation of the blade moves the housing and the implant magazine along the longitudinal axis of the blade.

5. The cartridge of claim 4, wherein a proximal end of the housing has an aperture, the cartridge further comprising an extension screw having a head and a shaft disposed within the aperture of the housing, wherein the extension screw defines a lumen through the head and the shaft, and the blade is at least partially disposed within the lumen of the extension screw.

6. The cartridge of claim 5, wherein the aperture of the housing is internally threaded and the shaft of the extension screw is threaded and threadably connected to the aperture of the housing, and wherein the lumen of the extension screw has a noncircular cross-section in the head of the extension screw and the blade has a noncircular collar configured to engage the noncircular cross-section of the lumen.

7. The cartridge of claim 6, further comprising a blade lock having a flange and a longitudinal body extending distally from the flange, the flange defining a key-hole shaped aperture through which the blade is disposed, wherein the key-hole shaped aperture in the flange has a first portion with a first diameter and a second portion with a second diameter smaller than the first diameter.

8. The cartridge of claim 7, wherein the second diameter of the key-hole shaped aperture in the flange is smaller than an outer diameter of the collar of the blade, and the first diameter of the key-hole shaped aperture in the flange is larger than the outer diameter of the collar of the blade.

9. The cartridge of claim 7, wherein the proximal end of the housing has a non-circular aperture, and wherein the longitudinal body of the blade lock has a non-circular cross-section along at least a portion of its length that is substantially matched to the non-circular aperture.

10. The cartridge of claim 9, wherein the non-circular cross section of the body of the blade lock is defined by a circumferential arc and a V-shaped notch.

11. The cartridge of claim 4, wherein the base of the implant magazine includes external ribs for engagement with recesses inside the outer housing of the cartridge.

12. The cartridge of claim 4, wherein a wedge of the blade is configured to engage a similarly configured recess in the head of the implant to temporarily hold the implant to the blade.

13. A kit comprising:
a driver;
a motor; and
the cartridge of claim 4 configured for cooperation with the driver to be operated by the motor.

14. The kit of claim 13, wherein the cartridge further comprises a magnet and the driver includes an analog hall sensor that communicates with the magnet to detect the location of the housing with respect to a cavity of the driver.

15. A method of using a driver, the method comprising:
loading an implant magazine having a plurality of implants into a housing of a cartridge, the implant magazine including an implant carrier defining a plurality of apertures, each implant of the plurality of implants being disposed within an aperture of the plurality of apertures;
operating a driver to control the cartridge such that a distal end of a blade of the cartridge is advanced distally relative to the housing of the cartridge and into engagement with a first implant of the plurality of implants located in a first aperture of the plurality of apertures;
inserting the first implant into a medium; and
withdrawing the distal end of the blade proximally relative to the housing and through the first aperture to allow the implant carrier to rotate about a central axis thereof until a next adjacent aperture of the plurality of apertures is located distally in front of the blade, wherein the step of withdrawing further includes allowing the implant carrier to rotate under the force of an indexing spring.

16. The method of claim 15, wherein the step of operating further includes deforming one or more fins defining the first aperture of the implant carrier by applying a predetermined force to the first implant from the distal end of the blade.

17. The method of claim 15, further comprising:
repeating, until a last of the plurality of implants is inserted into a medium, a sequence of:
operating the driver to control the cartridge such that the distal end of the blade is advanced distally relative to the housing of the cartridge and into engagement with a next adjacent implant of the plurality of implants located in the next adjacent aperture of the plurality of apertures;
inserting the next adjacent implant into a medium; and
withdrawing the distal end of the blade proximally relative to the housing and through the next adjacent aperture to allow the implant carrier to rotate about the central axis thereof until a next adjacent aperture of the plurality of apertures is located distally in front of the blade,
wherein the force of the indexing spring permits rotation of the implant carrier about substantially one complete revolution of the implant carrier.

18. A method of using a driver, the method comprising:
loading an implant magazine having a plurality of implants into a housing of a cartridge, the implant magazine including an implant carrier defining a plurality of apertures, each implant of the plurality of implants being disposed within an aperture of the plurality of apertures;
operating a driver to control the cartridge such that a distal end of a blade of the cartridge is advanced distally relative to the housing of the cartridge and into engagement with a first implant of the plurality of implants located in a first aperture of the plurality of apertures;
inserting the first implant into a medium; and
withdrawing the distal end of the blade proximally relative to the housing and through the first aperture to allow the implant carrier to rotate about a central axis thereof until a next adjacent aperture of the plurality of apertures is located distally in front of the blade,
wherein the step of operating the driver advances the distal end of the blade distally relative to the housing into contact with a surface of the implant magazine that is located proximally of the first implant in the first aperture to guide the distal end of the blade toward a center of the first aperture.

* * * * *